United States Patent
Kataoka et al.

(10) Patent No.: US 11,241,020 B2
(45) Date of Patent: *Feb. 8, 2022

(54) POWDERIZING AGENT FOR LIQUID COMPONENT

(71) Applicant: The Nisshin OilliO Group, Ltd., Tokyo (JP)

(72) Inventors: Yutaro Kataoka, Yokohama (JP); Seiya Takeguchi, Yokohama (JP); Tetsuro Iwasawa, Yokohama (JP); Shin Arimoto, Yokohama (JP); Hidetaka Uehara, Yokohama (JP)

(73) Assignee: THE NISSHIN OILLIO GROUP, LTD., Tokyo (JP)

( * ) Notice: Subject to any disclaimer, the term of this patent is extended or adjusted under 35 U.S.C. 154(b) by 7 days.

This patent is subject to a terminal disclaimer.

(21) Appl. No.: 16/071,796

(22) PCT Filed: Jan. 20, 2017

(86) PCT No.: PCT/JP2017/001953
§ 371 (c)(1),
(2) Date: Jul. 20, 2018

(87) PCT Pub. No.: WO2017/126667
PCT Pub. Date: Jul. 27, 2017

(65) Prior Publication Data
US 2019/0021359 A1    Jan. 24, 2019

(30) Foreign Application Priority Data

Jan. 21, 2016 (JP) .............................. JP2016-010107

(51) Int. Cl.
*A23D 9/02* (2006.01)
*A23L 2/62* (2006.01)
(Continued)

(52) U.S. Cl.
CPC ................. *A23D 9/02* (2013.01); *A23D 9/00* (2013.01); *A23L 2/38* (2013.01); *A23L 2/50* (2013.01);
(Continued)

(58) Field of Classification Search
CPC .. A23D 9/00; C11B 9/00; C11B 15/00; A23L 2/38; A23L 2/50; A23L 2/62
See application file for complete search history.

(56) References Cited

U.S. PATENT DOCUMENTS

| 3,796,816 A | 3/1974 | Hasman et al. |
| 4,877,636 A | 10/1989 | Kovano et al. |

(Continued)

FOREIGN PATENT DOCUMENTS

| CA | 2922936 A1 | 3/2015 |
| CN | 101909453 A | 12/2010 |

(Continued)

OTHER PUBLICATIONS

Japanese Patent Office Publication, Hyoujun Gijutsu-Shu, 2006 (Flavors), 2-2 Processing Techniques for Flavors, 2-2-2 Powders and Granules, Published on Mar. 14, 2007, pp. 328-330 (4 pages including partial English translation).

(Continued)

*Primary Examiner* — Erik Kashnikow
*Assistant Examiner* — Assaf Zilbering
(74) *Attorney, Agent, or Firm* — Buchanan Ingersoll & Rooney PC

(57) ABSTRACT

Provided is means of powderizing a liquid component, wherein
the powderizing agent contains an oil and/or fat composition,
the oil and/or fat composition contains an oil and/or fat component which contains one or more types of XXX-
(Continued)

Example 1    Example 2    Example 3 type triglycerides having fatty acid residues X, each with x carbon atoms, at positions 1 to 3 of glycerin, x, the number of carbon atoms, is an integer selected from 10 to 22, and the XXX-type triglyceride is contained at 50% by mass or more relative to a content of the oil and/or fat component being 100% by mass; or the powderizing agent, wherein the oil and/or fat composition is a powder oil and/or fat composition having a loose bulk density of 0.05 to 0.6 g/cm$^3$, the oil and/or fat component contains a β-type oil and/or fat, and a particle of the powder oil and/or fat composition has a plate shape.

20 Claims, 4 Drawing Sheets

(51) Int. Cl.
| | |
|---|---|
| A23D 9/00 | (2006.01) |
| A23L 2/50 | (2006.01) |
| C11B 9/00 | (2006.01) |
| A23L 2/38 | (2021.01) |
| C11B 15/00 | (2006.01) |
| C11C 3/00 | (2006.01) |
| A61K 8/67 | (2006.01) |
| A61K 8/37 | (2006.01) |

(52) U.S. Cl.
CPC ........ *A23L 2/62* (2013.01); *A61K 8/37* (2013.01); *A61K 8/67* (2013.01); *C11B 9/00* (2013.01); *C11B 15/00* (2013.01); *C11C 3/00* (2013.01)

(56) References Cited

U.S. PATENT DOCUMENTS

| | | | |
|---|---|---|---|
| 5,514,406 A | 5/1996 | Aoe et al. | |
| 6,090,598 A | 7/2000 | Yamaguchi et al. | |
| 8,535,749 B2 | 9/2013 | Kikuchi et al. | |
| 9,695,384 B2 | 7/2017 | Schweitzer et al. | |
| 2006/0115882 A1 | 6/2006 | Negishi et al. | |
| 2008/0089981 A1 | 4/2008 | Butler et al. | |
| 2010/0104694 A1 | 4/2010 | Schweitzer et al. | |
| 2010/0278985 A1 | 11/2010 | Kikuchi et al. | |
| 2011/0052771 A1 | 3/2011 | Rumbaut et al. | |
| 2011/0200734 A1 | 8/2011 | Nosaka et al. | |
| 2011/0223225 A1 | 9/2011 | Mezzenga et al. | |
| 2011/0318453 A1 | 12/2011 | Suganuma et al. | |
| 2013/0230634 A1 | 9/2013 | Arai et al. | |
| 2016/0213020 A1 | 7/2016 | Oonishi | |
| 2017/0208829 A1 | 7/2017 | Oonishi et al. | |
| 2017/0267945 A1 | 9/2017 | Schweitzer et al. | |
| 2018/0027838 A1 | 2/2018 | Suzuki et al. | |
| 2018/0035688 A1 | 2/2018 | Oonishi et al. | |
| 2018/0042259 A1 | 2/2018 | Oonishi et al. | |
| 2018/0161301 A1 | 6/2018 | Nosaka et al. | |
| 2018/0249729 A1 | 9/2018 | Kataoka et al. | |
| 2018/0256531 A1 | 9/2018 | Nosaka et al. | |
| 2019/0021355 A1 | 1/2019 | Takeguchi et al. | |
| 2019/0029283 A1 | 1/2019 | Kataoka et al. | |
| 2019/0031976 A1 | 1/2019 | Takeguchi et al. | |

FOREIGN PATENT DOCUMENTS

| | | |
|---|---|---|
| CN | 102421883 A | 4/2012 |
| CN | 103402364 A | 11/2013 |
| CN | 106536696 A | 3/2017 |
| CN | 107249344 A | 10/2017 |
| CN | 107249346 A | 10/2017 |
| CN | 107404893 A | 11/2017 |
| CN | 108024550 A | 5/2018 |
| DE | 28 32 636 A1 | 3/1980 |
| EP | 0209327 A2 | 1/1987 |
| EP | 0 536 824 B1 | 11/1995 |
| EP | 1776870 B1 | 7/2011 |
| EP | 2 622 966 A1 | 8/2013 |
| EP | 2839750 A1 | 2/2015 |
| EP | 3 173 464 A1 | 5/2017 |
| EP | 3 262 948 A1 | 1/2018 |
| EP | 3 262 949 A1 | 1/2018 |
| GB | 879 211 A | 10/1961 |
| GB | 1 316 079 A | 5/1973 |
| GB | 1564363 A * | 4/1980 ............... A23G 1/56 |
| JP | 52-071390 A | 6/1977 |
| JP | 63-240745 A | 10/1988 |
| JP | H-02-299544 A | 12/1990 |
| JP | 03-287880 A | 12/1991 |
| JP | 05-137506 A | 6/1993 |
| JP | 06-033087 A | 2/1994 |
| JP | 06-245700 A | 9/1994 |
| JP | H-08-27 B2 | 1/1996 |
| JP | 08-205773 A | 8/1996 |
| JP | 3083967 B2 | 8/1996 |
| JP | 2646422 B2 | 8/1997 |
| JP | 2700377 B2 | 1/1998 |
| JP | 10-295307 A | 11/1998 |
| JP | 03083967 B2 | 9/2000 |
| JP | 2002539782 A | 11/2002 |
| JP | 2003135001 A | 5/2003 |
| JP | 2005073610 A | 3/2005 |
| JP | 2005-350660 A | 12/2005 |
| JP | 2006-000087 A | 1/2006 |
| JP | 2006-109731 A | 4/2006 |
| JP | 3817450 B2 | 9/2006 |
| JP | 2007236289 A | 9/2007 |
| JP | 2007-289116 A | 11/2007 |
| JP | 2009-249614 A | 10/2009 |
| JP | 4352103 B2 | 10/2009 |
| JP | 2012-157370 A | 8/2012 |
| JP | 2012249617 A | 12/2012 |
| JP | 5501764 B2 | 5/2014 |
| JP | 2014124093 A | 7/2014 |
| JP | 2014-212731 A | 11/2014 |
| JP | 2015070837 A | 4/2015 |
| WO | 2005005586 A1 | 1/2005 |
| WO | 2008104381 A1 | 9/2008 |
| WO | 2008123946 A1 | 10/2008 |
| WO | WO 2010/052847 A1 | 5/2010 |
| WO | 2011134627 A1 | 11/2011 |
| WO | 2012043548 A1 | 4/2012 |
| WO | 2012/169457 A1 | 12/2012 |
| WO | 2014/069218 A1 | 5/2014 |
| WO | 2014087724 A1 | 6/2014 |
| WO | WO 2016/013582 A1 | 1/2016 |

OTHER PUBLICATIONS

International Search Report (PCT/ISA/210) dated Mar. 7, 2017, by the Japanese Patent Office as the International Searching Authority for International Application No. PCT/JP2017/001953.

Written Opinion (PCT/ISA/237) dated Mar. 7, 2017, by the Japanese Patent Office as the International Searching Authority for International Application No. PCT/JP2017/001953.

Office Action dated Jun. 14, 2017, by the Japanese Patent Office for Application No. 2017-522697.

Ciftci et al.: "Formation of solid lipid microparticles from fully hydrogenated canola oil using supercritical carbon dioxide," Journal of Food Engineering, Barking, Essex, GB, vol. 178, Jan. 19, 2016, pp. 137-144, XP029431886.

Millqvist-Fureby: "Characterisation of spray-dried emulsions with mixed fat phases," Colloids and Surfaces. B, Biointerfaces, vol. 31, No. 1-4, Sep. 1, 2003, pp. 65-79, XP55614221, NL.

Nolen: "Biological Evaluation of Hydrogenated Rapeseed Oil," Journal of The American Oil Chemists' Society (JAOCS), vol. 58, No. 1, Jan. 1, 1981, pp. 31-37, XP55614258, DE.

(56) References Cited

OTHER PUBLICATIONS

Extended Search Report issued by the European Patent Office in corresponding European Patent Application No. 17741544.5-1105 dated Aug. 30, 2019 (7 pages).
The extended European Search Report dated Aug. 14, 2019, by the European Patent Office in European Patent Application No. 17741542.9. (7 pages).
International Search Report (PCT/ISA/210) and the Written Opinion of the International Searching Authority (Form PCT/ISA/237) dated Mar. 7, 2017, by the Japanese Patent Office in the International Application No. PCT/JP2017/001951. (9 pages).
Office Action dated Jun. 14, 2017, by the Japanese Patent Office in Japanese Patent Application No. 2017-522695. (2 pages).
Apha F A C Gardner: "LOVIBOND 5.25" CELL Fatty Acid Specifications Typical Fatty Acid Composition % Packing", Nov. 19, 2008, XP055615791 (1 page).
The extended European Search Report dated Sep. 9, 2019, by the European Patent Office in European Patent Application No. 17741543.7 (8 pages).
International Search Report (PCT/ISA/210) and the Written Opinion of the International Searching Authority (Form PCT/ISA/237) dated Mar. 7, 2017, by the Japanese Patent Office in the International Application No. PCT/JP2017/001952. (7 pages).
Office Action (First Office Action ) dated Apr. 28, 2020, by the State Intellectual Property Office of People's Republic of China in Chinese Patent Application No. 201780007669.5 and an English Translation of the Office Action. (17 pages).
The First Office Action dated Apr. 8, 2020, by the State Intellectual Property Office of People's Republic of China in Chinese Patent Application No. 201780007637.5, and an English translation of the Office Action. (21 pages).
The extended European Search Report dated Jan. 24, 2020, by the European Patent Office in European Patent Application No. 17741545.2. (11 pages).
International Search Report (PCT/ISA/210) and the Written Opinion of the International Searching Authority (Form PCT/ISA/237) dated Mar. 7, 2017, by the Japanese Patent Office in the International Application No. PCT/JP2017/001954. (9 pages).
Office Action dated Oct. 20, 2020, by the U.S. Patent and Trademark Office in U.S. Appl. No. 15/762,971. (10 pages).
Ribeiro et al., "Crystallization modifiers in lipid systems," Journal of Food Science and Technology, Jul. 2015, vol. 52, No. 7, pp. 3925-3946.
Kang et al., "Refined cottonseed oil as a replacement for soybean oil in broiler diet," Food Science and Nutrition, Feb. 2019, vol. 7, No. 3, pp. 1027-1034.
Communication pursuant to Article 94(3) EPC dated May 11, 2021, by the European Patent Office in European Patent Application No. 16755551.5. (5 pages).
Office Action dated Jun. 8, 2021, by the U.S. Patent and Trademark Office in U.S. Appl. No. 15/553,906. (10 pages).
Office Action dated Feb. 3, 2021, by the U.S. Patent and Trademark Office in U.S. Appl. No. 15/553,640. (11 pages).
Office Action dated Feb. 4, 2021, by the U.S. Patent and Trademark Office in U.S. Appl. No. 16/071,746. (13 pages).
Office Action dated Mar. 12, 2021, by the U.S. Patent and Trademark Office in U.S. Appl. No. 15/762,971. (7 pages).
Office Action dated Mar. 18, 2021, by the U.S. Patent and Trademark Office in U.S. Appl. No. 15/553,771. (8 pages).
International Search Report (PCT/ISA/210) dated Oct. 27, 2015, by the Japanese Patent Office as the International Searching Authority for International Application No. PCT/JP2015/070850.
Written Opinion (PCT/ISA/237) dated Oct. 27, 2015, by the Japanese Patent Office as the International Searching Authority for International Application No. PCT/JP2015/070850.
International Search Report (PCT/ISA/210) dated Dec. 6, 2016, by the Japanese Patent Office as the International Searching Authority for International Application No. PCT/JP2016/078122.
Written Opinion (PCT/ISA/237) dated Dec. 6, 2016, by the Japanese Patent Office as the International Searching Authority for International Application No. PCT/JP2016/078122.
International Search Report (PCT/ISA/210) dated May 10, 2016, by the Japanese Patent Office as the International Searching Authority for International Application No. PCT/JP2016/055420.
Written Opinion (PCT/ISA/237) dated May 10, 2016, by the Japanese Patent Office as the International Searching Authority for International Application No. PCT/JP2016/055420.
International Search Report (PCT/ISA/210) dated May 10, 2016, by the Japanese Patent Office as the International Searching Authority for International Application No. PCT/JP2016/055421.
Written Opinion (PCT/ISA/237) dated May 10, 2016, by the Japanese Patent Office as the International Searching Authority for International Application No. PCT/JP2016/055421.
International Search Report (PCT/ISA/210) dated May 10, 2016, by the Japanese Patent Office as the International Searching Authority for International Application No. PCT/JP2016/055422.
Written Opinion (PCT/ISA/237) dated May 10, 2016, by the Japanese Patent Office as the International Searching Authority for International Application No. PCT/JP2016/055422.
Extended Search Report dated Nov. 23, 2017, by the European Patent Office in European Patent Application No. 15824376.6 (9 pages).
Communication pursuant to Article 94(3) EPC issued by the European Patent Office in European Patent Application No. 15824376.6-1105 dated Jan. 8, 2019 (6 pages).
Extended Search Report issued by the European Patent Office in European Patent Application No. 16755552.3-1106 dated Jul. 17, 2018 (8 pages).
Extended Search Report issued by the European Patent Office in European Patent Application No. 16755551.5-1105 dated Sep. 20, 2018 (9 pages).
Communication pursuant to Article 94(3) EPC issued by the European Patent Office in European Patent Application No. 16755551.5-1105 dated Aug. 23, 2019 (5 pages).
Extended Search Report issued by the European Patent Office in European Patent Application No. 16755550.7-1105 dated Aug. 6, 2018 (9 pages).
Extended Search Report issued by the European Patent Office in European Patent Application No. 16848698.3-1106 dated May 22, 2019.
The First Office Action issued by The State Intellectual Property Office of People's Republic of China in Chinese Patent Application No. 201580040036.5 dated Mar. 28, 2010 (17 pages including partial English translation).
Office Action dated Dec. 25, 2019, by the State Intellectual Property Office of the People's Republic of China in Chinese Patent Application No. 201680012188.9 and an English translation of the Office Action. (17 pages).
First Office Action dated Feb. 27, 2020, by The State Intellectual Property Office of People's Republic of China in Chinese Patent Application No. 201680012214.8, with an English translation of the Office Action. (17 pages).
Amir et al., "Interesterification of fats and oils—A Review". Pak. J. Food Sci., 22(3), pp. 143-153. (Year: 2012).
Ishikawa et al.: "Polymorphic Behavior of Palm Oil and Modified Palm Oils", Food Science and Technology International, (Jan. 1, 1997), vol. 3, No. 1, pp. 77-81, XP002716821.
Kebakile, "The Production of a High Free-Fat Whole Milk Powder for the Chocolate Industry; The Spray Chilling Technology" Thesis, Massey University (1996) (111 pages).
Lipp et al.: "Review of cocoa butter and alternative fats for use in chocolate—Part A. Compositional data," Food Chemistry, Elsevier LTD, NL, vol. 62, No. 1, Jan. 1, 1998, pp. 73-97.
Office Action issued by the U.S. Patent and Trademark Office in U.S. Appl. No. 15/553,906, dated Mar. 30, 2020, U.S. Patent and Trademark Office, Alexandria, VA. (18 pages).
Office Action issued by the U.S. Patent and Trademark Office in U.S. Appl. No. 15/553,640, dated Jun. 26, 2020, U.S. Patent and Trademark Office, Alexandria, VA. (8 pages).

(56) References Cited

OTHER PUBLICATIONS

Office Action issued by the U.S. Patent and Trademark Office in U.S. Appl. No. 15/327,734, dated Sep. 6, 2019, U.S. Patent and Trademark Office, Alexandria, VA. (8 pages).

Office Action issued by the U.S. Patent and Trademark Office in U.S. Appl. No. 15/553,771, dated Sep. 16, 2020, U.S. Patent and Trademark Office, Alexandria, VA. (8 pages).

Office Action issued by the U.S. Patent and Trademark Office in U.S. Appl. No. 15/553,640, dated Nov. 1, 2019, U.S. Patent and Trademark Office, Alexandria, VA. (8 pages).

Office Action issued by the U.S. Patent and Trademark Office in U.S. Appl. No. 15/553,906, dated Aug. 30, 2019, U.S. Patent and Trademark Office, Alexandria, VA. (17 pages).

Office Action issued by the U.S. Patent and Trademark Office in U.S. Appl. No. 15/553,906, dated Sep. 22, 2020, U.S. Patent and Trademark Office, Alexandria, VA. (23 pages).

Office Action issued by the U.S. Patent and Trademark Office in U.S. Appl. No. 16/071,830, dated Oct. 7, 2020, U.S. Patent and Trademark Office, Alexandria, VA. (9 pages).

Office Action dated Apr. 1, 2021, by the U.S. Patent and Trademark Office in U.S. Appl. No. 16/071,734. (12 pages).

Office Action dated Apr. 1, 2021, by the U.S. Patent and Trademark Office in U.S. Appl. No. 16/071,830. (7 pages).

Notice of Allowance dated Sep. 27, 2021, by the U.S. Patent and Trademark Office in U.S. Appl. No. 16/071,734. (9 pages).

Notice of Allowance dated Aug. 4, 2021, by the U.S. Patent and Trademark Office in U.S. Appl. No. 15/762,971. (9 pages).

Notice of Allowance dated Sep. 22, 2021, by the U.S. Patent and Trademark Office in U.S. Appl. No. 16/071,746. (9 pages).

Notice of Allowance dated Oct. 1, 2021, by the U.S. Patent and Trademark Office in U.S. Appl. No. 16/071,830. (9 pages).

\* cited by examiner

Example 1      Example 2      Example 3

Example 4      Example 5      Example 6

Example 7    Example 8    Example 9

Example 10    Example 11    Example 12

Example 13   Example 14   Example 15

Example 16   Example 17   Example 18

Example 19   Example 20   Example 21   Example 22   Example 23

POWDERIZING AGENT FOR LIQUID COMPONENT

TECHNICAL FIELD

The present invention relates to, for example, a powderizing agent for a liquid component and a method of producing a powder composition using the powderizing agent.

BACKGROUND ART

Products such as foods and/or beverages, cosmetics, and pharmaceutical drugs are blended with various functional materials.

Many of these products contain functional materials as liquid components, such as liquid foods, liquid cosmetics, and liquid-filled capsules. Because of the liquid form, when blended in products such as foods and/or beverages, these liquid components often face up to a limitation in terms of the amount blended and also difficulty in the blending method.

In light of the above, conventional techniques powderize the liquid components. Powderization not only improves miscibility into products but also contributes to the improvement of the storage stability and instant solubility of functional materials. For these reasons, powderization of liquid components provides great advantages (Non Patent Literature 1).

Here, for example, known methods of powderizing a liquid component include a method including adding an emulsifier, maltotriose, and water to an oil-soluble component to prepare an emulsified mixture and then spray drying this emulsified mixture (Patent Literature 1).

Instead of the spray drying method, known methods also include a method including heating and melting an oil and/or fat having a high melting point and then powderizing the liquid component by a spray cooling method (Patent Literature 2).

CITATION LIST

Patent Literatures

Patent Literature 1: Japanese Patent Application Publication No. 2006-87
Patent Literature 2: Japanese Patent Application Publication No. 2014-212731

Non Patent Literature

Non Patent Literature 1: Japanese Patent Office Publication, Hyoujun Gijutsu-Shu, 2006 (Flavors), 2-2 Processing Techniques for Flavors, 2-2-2 Powders and Granules, Published on Mar. 14, 2007

SUMMARY OF INVENTION

Technical Problems

However, there is a problem that since a heating operation is performed in the spray drying method, a heat sensitive liquid component evaporates or deteriorates due to oxidation, for example.

In addition, the spray cooling method requires a dedicated apparatus for flow rate control or high speed rotation and further requires a high level of expertise of the operator.

The present inventors identified the problems described above and further recognized that it was necessary to develop a method which makes it possible for anyone to easily powderize even a heat sensitive liquid component without the necessity of a special apparatus or skills.

Solution to Problems

The present inventors have made earnest studies on the above problems to find that use of an oil and/or fat composition containing a triglyceride having a particular structure in a particular composition makes it possible for anyone to easily powderize functional materials, conventionally used in the liquid form, by a process simpler than conventional ones. The present invention has been made based on this finding.

To be more specific, the present invention relates to the following:

[1] A powderizing agent for a liquid component, wherein
  the powderizing agent contains an oil and/or fat composition,
  the oil and/or fat composition contains an oil and/or fat component which contains one or more types of XXX-type triglycerides having fatty acid residues X, each with x carbon atoms, at positions 1 to 3 of glycerin,
  x, the number of carbon atoms, is an integer selected from 10 to 22, and
  the XXX-type triglyceride is contained at 50% by mass or more relative to a content of the oil and/or fat component being 100% by mass.
[2] The powderizing agent according to [1] described above, wherein
  the oil and/or fat composition is a powdered oil and/or fat composition,
  the oil and/or fat component contains a β-type oil and/or fat,
  a particle of the powder oil and/or fat composition has a plate shape, and
  a loose bulk density of the powder oil and/or fat composition is 0.05 to 0.6 g/cm$^3$.
[3] The powderizing agent according to [1] or [2] described above, wherein
  the liquid component contains a hydrophobic substance.
[4] The powderizing agent according to any one of [1] to [3] described above, wherein
  the liquid component is a solution of a hydrophobic substance.
[5] The powderizing agent according to [4] described above, wherein
  a solvent of the solution is selected from the group consisting of liquid oils, alcohols, organic solvents, and mixtures thereof.
[6] The powderizing agent according to any one of [1] to [3] described above, wherein
  the liquid component is an emulsion of a hydrophobic substance.
[7] The powderizing agent according to [6] described above, wherein
  the emulsion of a hydrophobic substance contains at least one selected from the group consisting of water, emulsifiers, and glycerin.
[8] The powderizing agent according to any one of [3] to [7] described above, wherein
  the hydrophobic substance is selected from the group consisting of flavors, dyes, vitamins, lipids, and mixtures thereof.

[9] The powderizing agent according to [1] or [2] described above, wherein
the liquid component contains a hydrophilic substance.
[10] The powderizing agent according to [1], [2], or [9] described above, wherein
the liquid component is a solution of a hydrophilic substance.
[11] The powderizing agent according to [10] described above, wherein
a solvent of the solution is selected from the group consisting of water, alcohols, organic solvents, and mixtures thereof.
[12] The powderizing agent according to [1], [2], or [9] described above, wherein
the liquid component is an emulsion of a hydrophilic substance.
[13] The powderizing agent according to [12] described above, wherein
the emulsion of a hydrophilic substance contains at least one selected from the group consisting of water, emulsifiers, and glycerin.
[14] The powderizing agent according to any one of [9] to [13] described above, wherein
the hydrophilic substance is selected from the group consisting of flavors, dyes, vitamins, and mixtures thereof.
[15] The powderizing agent according to any one of [1] to [14] described above, wherein
the liquid component is a liquid food.
[16] The powderizing agent according to [15] described above, wherein
the liquid food is selected from the group consisting of cow's milk, wines, fruit juices, stock, and yogurts.
[17] A method of producing a powder composition, comprising:
a mixing step of mixing the powderizing agent according to any one of [1] to [16] described above and a liquid component.
[18] The production method according to [17] described above, further comprising a cooling step of cooling a mixture of the powderizing agent and the liquid component.
[19] The production method according to [18] described above, wherein
a cooling temperature in the cooling step is equal to or higher than a temperature calculated by the following formula:

cooling temperature (° C.)=number of carbon atoms $x \times 6.6-68$.

[20] The production method according to [19] described above, wherein
the oil and/or fat component contains a β-type oil and/or fat, and
the cooling temperature is a temperature lower than a melting point of the β-type oil and/or fat.
[21] The production method according to any one of [18] to [20] described above, wherein
a seeding process, a tempering process, and/or a pre-cooling process are further performed between the mixing step and the cooling step.
[22] The production method according to any one of [17] to [21] described above, wherein
an amount of the liquid component used is 0.1 to 30% by mass relative to a total mass of the powder composition.
[23] A powder composition produced by the production method according to any one of [17] to [22] described above.

[24] A powder composition comprising the powderizing agent according to any one of [1] to [16] described above.
[25] The powder composition according to [24] described above for use as a raw material or an intermediate of a product.
[26] The powder composition according to [25] described above, wherein
the product is selected from the group consisting of foods and/or beverages, cosmetics, quasi drugs, pharmaceutical drugs, household goods, feeds, general goods, agricultural chemicals, and industrial chemical products.
[27] A food and/or beverage comprising the powder composition according to any one of [23] to [26] described above.
[28] The food and/or beverage according to [27] described above, being a luxury food.
[29] A method of powderizing a liquid component, comprising a step of mixing the powderizing agent according to any one of [1] to [16] described above and a liquid component.
[30] The method according to [29] described above, further comprising a cooling step of cooling a mixture of the powderizing agent and the liquid component.
[31] A powder composition powderized by the method according to [29] or [30] described above.

Advantageous Effects of Invention

As shown in Examples to be described later, a powderizing agent of the present invention can powderize functional materials, conventionally used in the liquid form, by a process simpler than conventional ones. In addition, since excessive heating is unnecessary in the powderization in accordance with the present invention, it is possible to powderize even a heat sensitive liquid component without the necessity of a special apparatus or skills.

Thus, the present invention can provide a product which is excellent in handleability at the time of manufacturing the product and in consumer convenience at the time of using the product.

DESCRIPTION OF EMBODIMENTS

Figure 1:
FIG. 1 is a view illustrating powder compositions obtained in Examples 1 to 3.

<Powderizing Agent for Liquid Component>
A "powderizing agent for a liquid component" of the present invention (hereinafter also referred to as a "powderizing agent") contains an oil and/or fat composition described below as an essential component.

<Oil and/or Fat Composition>

The oil and/or fat composition of the present invention is a liquid oil and/or fat composition in the molten state, containing an oil and/or fat component which contains one or more types of XXX-type triglycerides having fatty acid residues X, each with x carbon atoms, at positions 1 to 3 of glycerin, in which x, the number of carbon atoms, is an integer selected from 10 to 22, and the XXX-type triglyceride is contained at 50% by mass or more relative to the content of the oil and/or fat component being 100% by mass.

In addition, the oil and/or fat composition of the present invention is also a powdered oil and/or fat composition (hereinafter also referred to as a powder oil and/or fat composition) produced from the above-described liquid oil and/or fat composition, being a powdered oil and/or fat composition in the solid state, in which the oil and/or fat component contains a β-type oil and/or fat, a particle of the powder oil and/or fat composition has a plate shape, and a loose bulk density of the powder oil and/or fat composition is 0.05 to 0.6 g/cm$^3$.

Hereinafter, a description is provided in detail for the oil and/or fat composition used in the powderizing agent of the present invention (focusing particularly on the powdered oil and/or fat composition).

<Oil and/or Fat Component>

Whether in the liquid form or in the powder form, the oil and/or fat composition of the present invention contains an oil and/or fat component. The oil and/or fat component at least contains a XXX-type triglyceride and optionally other triglycerides.

If the oil and/or fat composition of the present invention is in the powder form, the oil and/or fat component described above contains a β-type oil and/or fat. Here, the β-type oil and/or fat is an oil and/or fat made up only of a β-type crystal, which is one of the crystal polymorphism of oils and/or fats. Other oils and/or fats of the crystal polymorphism include a β'-type oil and/or fat and an α-type oil and/or fat. The β'-type oil and/or fat is an oil and/or fat made up only of a β'-type crystal, which is one of the crystal polymorphism of oils and/or fats. The α-type oil and/or fat is an oil and/or fat made up only of an α-type crystal, which is one of the crystal polymorphism of oils and/or fats. Some oil and/or fat crystals have different sub lattice structures (crystalline structures) despite identical compositions, which is called crystal polymorphism. There are typically a hexagonal type, an orthorhombic type, and a triclinic type, and they are called an α-type, a R'-type, and a β-type, respectively. In addition, regarding the melting points of the polymorphs, the melting points become higher in the order of α, β', and β, and the melting points of the polymorphs differ depending on the type of the fatty acid residue X having x carbon atoms. In light of this, Table 1 shows below the melting points of the polymorphs (° C.) in the cases of tricaprin, trilaurin, trimyristin, tripalmitin, tristearin, triarachidin, and tribehenin. Note that Table 1 was created based on Nissim Garti et al., "Crystallization and Polymorphism of Fats and Fatty Acids," Marcel Dekker Inc., 1988, pp. 32-33. Moreover, when creating Table 1, the temperature of the melting point (° C.) was rounded off to the nearest whole number. In addition, if the composition of an oil and/or fat and the melting points of the polymorphs are obtained, it is possible to detect at least whether or not the β-type oil and/or fat is present in the oil and/or fat.

TABLE 1

| | α-Type Oil and/or Fat (° C.) | β'-Type Oil and/or Fat (° C.) | β-Type Oil and/or Fat (° C.) |
|---|---|---|---|
| Tricaprin | −9 | 16 | 32 |
| Trilaurin | 15 | 34 | 47 |
| Trimyristin | 33 | 45 | 59 |
| Tripalmitin | 45 | 57 | 66 |
| Tristearin | 55 | 63 | 74 |
| Triarachidin | 62 | 69 | 78 |
| Tribehenin | 68 | 74 | 83 |

A general method of identifying these polymorphs includes an X-ray diffraction method, and the diffraction condition is given by Bragg's formula below.

$$2d \sin \theta = n\lambda (n=1,2,3 \ldots )$$

Diffraction peak appear at positions satisfying this formula. Here, d is a lattice constant, θ is a diffraction (incident) angle, λ is a wavelength of the X-ray, and n is a natural number. Within the range of diffraction peak 2θ=16 to 27° corresponding to short spacing, it is possible to obtain information on packing of the sides (sub lattice) in the crystal and thus to identify the polymorphs. Particularly in the case of triacylglycerols, a characteristic peak of the β-type appears at 2θ=19, 23, and 24° (near 4.6 Å, near 3.9 Å, and near 3.8 Å) and a characteristic peak of the α-type appears near 21° (4.2 Å). Note that regarding the X-ray diffraction measurement, the measurement is performed by using, for example, an X-ray diffractometer maintained at 20° C. (Rigaku Corporation, Horizontal Sample Mount X-ray Diffractometer Ultima IV). CuKα ray (1.54 Å) is used most often as the light source of X-ray.

Moreover, the crystal polymorphism of the oil and/or fat described above can be predicted by a differential scanning calorimetry method (DSC method). For example, the prediction of the β-type oil and/or fat is performed by predicting the crystalline structure of the oil and/or fat using a differential scanning calorimeter (manufactured by SII Nano-Technology Inc., product number BSC 6220) based on a DSC curve obtained by raising the temperature to 100° C. at a rate of temperature rise of 10° C./min.

Here, if the oil and/or fat composition of the present invention is in the powder form, the oil and/or fat component may be one containing the β-type oil and/or fat or one containing the β-type oil and/or fat as a main component (more than 50% by mass), and a preferable embodiment is such that the above-described oil and/or fat component is composed substantially of the β-type oil and/or fat, a more preferable embodiment is such that the above-described oil and/or fat component is composed of the β-type oil and/or fat, and a particularly preferable embodiment is such that the above-described oil and/or fat component is composed only of the β-type oil and/or fat. The case where all of the oil and/or fat components above are the β-type oil and/or fat is a case where the α-type oil and/or fat and/or the β'-type oil and/or fat is not detected by the differential scanning calorimetry method. Another preferable embodiment is the case where the oil and/or fat component (or the powder oil and/or fat composition containing the oil and/or fat component) has a diffraction peak near 4.5 to 4.7 Å and preferably near 4.6 Å in the X-ray diffraction measurement, but has no X-ray diffraction peak of the short spacing of the α-type oil and/or fat and/or β'-type oil and/or fat in Table 1, particularly no diffraction peak near 4.2 Å. In that case, it is possible to judge that all of the oil and/or fat components above are the β-type oil and/or fat. As a further embodiment of the present invention, all of the oil and/or fat component are preferably the β-type oil and/or fat but may contain other α-type oil and/or fat and β'-type oil and/or fat. Here, that the oil and/or fat component of the present invention "contains the β-type oil and/or fat" and an index of the relative amount of the β-type oil and/or fat to the α-type oil and/or fat+β-type oil and/or fat can be assumed from, among the X-ray diffraction peaks, the intensity ratio between the characteristic peak of the β-type and the characteristic peak of the α-type: [intensity of the characteristic peak of the β-type/(intensity of the characteristic peak of the α-type+intensity of the characteristic peak of the β-type)] (hereinafter also referred to as the peak intensity ratio). To be more specific, based on the knowledge concerning the X-ray diffraction measurement described above, the index representing the amount present of the β-type oil and/or fat of the oil and/or fat component is obtained by calculating the ratio between the peak intensity of 2θ=19° (4.6 Å) being the characteristic peak of the β-type and the peak intensity of 2θ=21° (4.2 Å) being the characteristic peak of the α-type: 19°/(19°+21°) [4.6 Å/(4.6 Å+4.2 Å)]. Thus, it can be understood that "the β-type oil and/or fat is contained." In the present invention, the all of the oil and/or fat components described above are preferably the β-type oil and/or fat (in other words, peak intensity ratio=1). For example, it is appropriate that the lower limit value of the peak intensity ratio is, for example, 0.4 or more, preferably 0.5 or more, more preferably 0.6 or more, further preferably 0.7 or more, particularly preferably 0.75 or more, and especially preferably 0.8 or more. If the peak intensity is 0.4 or more, it is possible to regard that the β-type oil and/or fat is the main component of more than 50% by mass. The upper limit value of the peak intensity ratio is preferably 1, but may be 0.99 or less, 0.98 or less, 0.95 or less, 0.93 or less, 0.90 or less, 0.85 or less, 0.80 or less, and the like. The peak intensity ratio can be any of the lower limit values and the upper limit values described above or any combination thereof.

<XXX-Type Triglyceride>

Whether in the liquid form or in the powder form, the oil and/or fat component of the present invention contains one or more types of XXX-type triglycerides having fatty acid residues X, each with x carbon atoms, at positions 1 to 3 of glycerin. The XXX-type triglyceride is a triglyceride having fatty acid residues X, each with x carbon atoms, at positions 1 to 3 of glycerin, and the fatty acid residues X are identical to each other. Here, the number of carbon atoms x is an integer selected from 10 to 22, preferably an integer selected from 12 to 22, more preferably an integer selected from 14 to 20, and further preferably an integer selected from 16 to 18.

The fatty acid residue X may be a saturated or unsaturated fatty acid residue. Specifically, the fatty acid residue X includes, but is not limited to, residues of capric acid, lauric acid, myristic acid, palmitic acid, stearic acid, arachidic acid, and behenic acid, for example. The fatty acid is more preferably lauric acid, myristic acid, palmitic acid, stearic acid, arachidic acid, and behenic acid, further preferably myristic acid, palmitic acid, stearic acid, and arachidic acid, and especially preferably palmitic acid and stearic acid.

When the total mass of the oil and/or fat component is set to 100% by mass, the content of the XXX-type triglyceride is a range having a lower limit of 50% by mass or more, preferably 60% by mass or more, more preferably 70% by mass or more, and further preferably 80% by mass or more, and an upper limit of, for example, 100% by mass or less, preferably 99% by mass or less, and more preferably 95% by mass or less. It is possible to use one type or two or more types, preferably one or two types of XXX-type triglycerides. One type is more preferably used. In the case of two or more types of XXX-type triglycerides, the total value thereof is the content of the XXX-type triglyceride.

<Other Triglycerides>

Whether in the liquid form or in the powder form, oil and/or fat component of the present invention may contain other triglycerides other than the XXX-type triglyceride described above as long as the effects of the present invention are not impaired. The other triglycerides may be multiple types of triglycerides or any of synthetic oils and/or fats and natural oils and/or fats. The synthetic oils and/or fats include glyceryl tricaprylate, and the like. The natural oils and/or fats include, for example, cocoa butter, sunflower oil, rapeseed oil, soybean oil, and cottonseed oil. When the total triglyceride content in the oil and/or fat component of the present invention is set to 100% by mass, no problem arises if the other triglycerides are contained at 1% by mass or more, for example about 5 to 50% by mass. The content of the other triglycerides is, for example, 0 to 30% by mass, preferably 0 to 18% by mass, more preferably 0 to 15% by mass, and further preferably 0 to 8% by mass.

<Other Components>

Whether in the liquid form or in the powder form, the oil and/or fat composition of the present invention may contain, in addition to the oil and/or fat component such as triglycerides described above, other optional components such as an emulsifier, a flavor, skim milk powder, whole milk powder, cocoa powder, sugar, and dextrin. The amount of these other components can be any amount as long as the effects of the present invention are not impaired. For example, when the total mass of the oil and/or fat composition is set to 100% by mass, the amount is 0 to 70% by mass, preferably 0 to 65% by mass, and more preferably 0 to 30% by mass. Preferably, 90% by mass or more of the other components is a powder body having an average particle diameter of 1000 μm or less and more preferably a powder body having an average particle diameter of 500 μm or less. Note that the average particle diameter mentioned here is a value measured by laser diffraction scattering method (ISO 133201 and ISO 9276-1).

Note that it is preferable that a preferable oil and/or fat composition of the present invention is substantially composed only of the oil and/or fat component and it is preferable that the oil and/or fat component is substantially composed only of the triglyceride. In addition, "substantially" means that the components other than the oil and/or fat component contained in the oil and/or fat composition or the components other than the triglyceride contained in the oil and/or fat component are, for example, 0 to 15% by mass, preferably 0 to 10% by mass, and more preferably 0 to 5% by mass when the oil and/or fat composition or the oil and/or fat component is set to 100% by mass.

<Powder Oil and/or Fat Composition>

Regarding the powder oil and/or fat composition of the present invention, without employing special processing means such as spraying or machine pulverization by a pulverizer such as a mill, it is possible to obtain a powdered oil and/or fat composition (powder oil and/or fat composition) by transforming into the molten state an oil and/or fat composition containing one or more types of XXX-type triglycerides having fatty acid residues X, each with x carbon atoms, at positions 1 to 3 of glycerin, keeping it at a particular cooling temperature, followed by cooling and solidification. To be more specific, a powder oil and/or fat composition containing the β-type oil and/or fat and having a plate-shaped particle shape is obtained by: (a) preparing an oil and/or fat composition containing the XXX-type triglyceride described above; heating, as an optional step (b), the oil and/or fat composition obtained in step (a) and dissolving the triglyceride contained in the oil and/or fat composition to obtain the oil and/or fat composition in the molten state; (d) and further cooling and solidifying the oil and/or fat composition. Note that it is also possible to produce the powder oil and/or fat composition by applying known pulverization processing means such as a hammermill and a cutter mill to the solid obtained after the cooling.

For example, the cooling of step (d) described above is performed on the oil and/or fat composition in the molten state at a temperature which is lower than the melting point of the β-type oil and/or fat of the oil and/or fat component contained in the oil and/or fat composition and which is equal to or higher than the cooling temperature obtained from the following formula:

cooling temperature (° C.)=number of carbon atoms x×6.6-68.

Cooling in such a temperature range makes it possible to efficiently produce the β-type oil and/or fat, followed by formation of fine crystal. Thus, it is possible to easily obtain a powder oil and/or fat composition. Note that "fine" described above refers to a case where the primary particle (crystal of the smallest size) is, for example, 20 μm or less, preferably 15 μm or less, and more preferably 10 μm. In addition, there is a case where if the cooling is not performed in such a temperature range, the β-type oil and/or fat is not produced and a solid is not formed which has voids with an increased volume larger than the oil and/or fat composition in the molten state. Moreover, in the present invention, the cooling is performed in such a temperature range to produce the β-type oil and/or fat while being left standing and the particles of the powder oil and/or fat composition are formed in the plate shape. The cooling method is useful in the identification of the powder oil and/or fat composition of the present invention.

<Characteristics of Powder Oil and/or Fat Composition>

The powder oil and/or fat composition of the present invention is a solid in the powder form at normal temperature (20° C.)

If substantially composed only of the oil and/or fat component, for example, the loose bulk density of the powder oil and/or fat composition of the present invention is 0.05 to 0.6 g/cm³, preferably 0.1 to 0.5 g/cm³, more preferably 0.15 to 0.4 g/cm³, and further preferably 0.2 to 0.3 g/cm³. Here, the "loose bulk density" is the bulk density in the state after a powder body has freely fallen. The measurement of the loose bulk density (g/cm³) can be obtained as follow. For example, a graduated cylinder having an inner diameter of 15 mm×25 mL is loosely filled with an appropriate amount of the powder oil and/or fat composition allowed to fall from about 2 cm above the upper open end of the graduated cylinder. Then, the packed mass (g) is measured and the volume (mL) is read. Finally, the mass (g) of the powder oil and/or fat composition per mL is calculated. In addition, the loose bulk density can be calculated by using a bulk specific gravity measurement apparatus of Kuramochi Kagakukikai Seisakusho and using a bulk specific gravity measured based on JIS K-6720 (or ISO 1060-1 and -2). To be more specific, 120 mL of sample is allowed to fall onto a receiver (100 mL cylindrical container having an inner diameter of 40 mm×height 85 mm) from a position higher by 38 mm than the upper open end of the receiver. A portion of the sample sticking out of the receiver is removed, and the mass (A g) of the sample corresponding to the internal volume of the receiver (100 mL) is weighed. The loose bulk density can be obtained by the following formula.

loose bulk density (g/mL)=A (g)/100 (mL)

It is preferable that the measurement is performed three times and the average value thereof is taken.

In addition, regarding the powder oil and/or fat composition of the present invention, the particle thereof usually has the form of a plate shape and has an average particle diameter (effective diameter) of, for example, 5 to 200 μm, preferably 10 to 150 μm, more preferably 20 to 120 μm, and especially preferably 25 to 100 μm. Here, the average particle diameter (effective diameter) can be obtained with a particle size distribution measurement apparatus (for example, Microtrac MT 3300 ExII manufactured by Nikkiso Co., Ltd.) based on the laser diffraction scattering method (ISO 133201 and ISO 9276-1). The effective diameter means the particle diameter of a spherical shape in the case where the actually measured diffraction pattern of the crystal being the measurement target matches the theoretical diffraction pattern assumed to be of the spherical shape. As described above, in the case of the laser diffraction scattering method, the theoretical diffraction pattern assumed to be of a spherical shape and the actually measured diffraction pattern are matched to each other to calculate the effective diameter. Thus, it is possible to perform measurement by the same principle even when the measurement target is of a plate shape or spherical shape. Here, regarding the plate shape, the aspect ratio is preferably 1.1 or more, the aspect ratio is more preferably 1.2 or more, and the aspect ratio is further preferably 1.2 to 3.0, particularly preferably 1.3 to 2.5, and especially preferably 1.4 to 2.0. Note that the aspect ratio mentioned here is defined to be a ratio between the longer side and the shorter side of a rectangle circumscribed around a particle figure such that the area thereof is smallest. In addition, if the particle has a spherical shape, the aspect ratio is smaller than 1.1. In the method of dissolving an oil and/or fat with a high solid fat content at normal temperature such as extremely hardened oil followed by direct spraying, which is a conventional technique, the particles of the powder oil and/or fat composition are formed into a spherical shape by surface tension, and the aspect ratio becomes less than 1.1. Additionally, the aspect ratio can be obtained as the average value with respect to the measured number by measuring the length of the longitudinal direction and the length in the latitudinal direction for arbitrarily selected particles by direct observation using, for example, an optical microscope or a scanning electron microscope.

<Method of Producing Powder Oil and/or Fat Composition>

The powder oil and/or fat composition of the present invention can be produced by a method including the following steps:

(a) a step of preparing an oil and/or fat composition containing a XXX-type triglyceride;

(b) an optional step of, for example, optionally heating the oil and/or fat composition obtained in step (a) and dissolving the triglyceride contained in the oil and/or fat composition to obtain the oil and/or fat composition in the molten state; and (d) a step of cooling and solidifying the oil and/or fat composition to obtain a powder oil and/or fat composition containing the β-type oil and/or fat and having a plate-shaped particle shape.

In addition, an optional step as step (c) for promoting powder generation, for example (c1) seeding step, (c2) a tempering step, and/or (c3) a pre-cooling step, may be included between steps (b) and (d) described above. Moreover, the powder oil and/or fat composition obtained in step (d) described above may be one obtained by step (e) of obtaining a powdered oil and/or fat composition through powderization of the solid obtained after the cooling of step (d). Hereinafter, a description is provided for steps (a) to (e) described above.

(a) Preparation Step

The oil and/or fat composition containing the XXX-type triglyceride prepared in step (a) can be produced based on the method of producing an oil and/or fat such as an ordinary XXX-type triglyceride which contains one or more types of XXX-type triglycerides having fatty acid residues X, each with x carbon atoms, at positions 1 to 3 of glycerin or can easily be obtained from the market. Here, the XXX-type triglyceride identified by the number of carbon atoms x and the fatty acid residues X described above is the same as that of the target oil and/or fat component finally obtained except for the crystal polymorphism. The oil and/or fat composition may contain the β-type oil and/or fat. For example, the content of the β-type oil and/or fat may be 0.1% by mass or less, 0.05% by mass or less, or 0.01% by mass or less. Note that since the β-type oil and/or fat disappears when the oil and/or fat composition is e.g. heated into the molten state, the oil and/or fat composition may be the oil and/or fat composition in the molten state. When in the molten state, for example, that the oil and/or fat composition does not substantially contain the β-type oil and/or fat also means the case where, in addition to the XXX-type triglyceride, substantially none of the oil and/or fat components is the β-type oil and/or fat. The presence of the β-type oil and/or fat can be confirmed by confirmation and the like of a diffraction peak attributed to the β-type oil and/or fat by the X-ray diffraction measurement or the β-type oil and/or fat by the differential scanning calorimetry method. The amount present of the β-type oil and/or fat in the case of "substantially not containing the β-type oil and/or fat" can be assumed from, among the X-ray diffraction peaks, the intensity ratio between the characteristic peak of the β-type and the characteristic peak of the α-type [intensity of the characteristic peak of the β-type/(intensity of the characteristic peak of the α-type+intensity of the characteristic peak of the β-type)] (peak intensity ratio). The peak intensity ratio of the oil and/or fat composition is, for example, 0.2 or less, preferably 0.15 or less, and more preferably 0.10 or less. The oil and/or fat composition may contain one type or two or more types, preferably one or two types, and more preferably one type of the XXX-type triglycerides as described above.

To be more specific, for example, the XXX-type triglyceride described above can be produced by direct synthesis using a fatty acid or a fatty acid derivative and glycerin. A method of directly synthesizing the XXX-type triglyceride includes (i) a method of directly esterifying a fatty acid having X carbon atoms and glycerin (direct ester synthesis), (ii) a method of reacting glycerin with a fatty acid alkyl (for example, a fatty acid methyl and a fatty acid ethyl), in which a carboxyl group of a fatty acid X having x carbon atoms is bonded to an alkoxyl group, under a condition of a basic or acidic catalyst (transesterification synthesis using a fatty acid alkyl), and (iii) a method of reacting glycerin with a fatty acid halide (for example, a fatty acid chloride and a fatty acid bromide), in which a hydroxyl group of a carboxyl group of the fatty acid X having x carbon atoms is substituted with a halogen, in the presence of a basic catalyst (acid halide synthesis).

Although the XXX-type triglyceride can be produced by any of the methods (i) to (iii) described above, (i) the direct ester synthesis or (ii) the transesterification synthesis using a fatty acid alkyl is preferable and (i) the direct ester synthesis is more preferable from the viewpoint of easiness of production.

In order to produce the XXX-type triglyceride by (i) the direct ester synthesis, the fatty acid X or the fatty acid Y is used preferably in 3 to 5 moles and is used more preferably in 3 to 4 moles relative to 1 mole of glycerin from the viewpoint of production efficiency.

The reaction temperature of the XXX-type triglyceride in (i) the direct ester synthesis may be a temperature which makes it possible to remove generation water generated by the esterification reaction to the outside of the system, and is preferably 120° C. to 300° C., more preferably 150° C. to 270° C., and further preferably 180° C. to 250° C., for example. If the reaction is performed at 180 to 250° C., it is possible to particularly efficiently produce the XXX-type triglyceride.

In (i) the direct ester synthesis of the XXX-type triglyceride, a catalyst which promotes esterification reaction may be used. The catalyst includes an acidic catalyst, an alkaline earth metal alkoxide, and the like. The amount of catalyst used is preferably about 0.001 to 1% by mass relative to the total mass of the reaction raw materials.

In (i) the direct ester synthesis of the XXX-type triglyceride, after the reaction, it is possible to remove the catalyst and the unreacted raw materials by performing known purification treatment such as water washing, alkali deacidification and/or pressure reducing deacidification, and adsorption treatment. Moreover, by implementing bleaching and deodorization treatment, it is possible to further purify the obtained reaction product.

When the total mass of all triglycerides contained in the oil and/or fat composition is set to 100% by mass, the amount of the XXX-type triglyceride contained in the oil and/or fat composition is 100 to 50% by mass, preferably 95 to 55% by mass, more preferably 90 to 60% by mass, and further especially preferably 85 to 65% by mass.

<Other Triglyceride>

Various triglycerides may be contained in addition to the XXX-type triglyceride described above as other triglycerides to be the oil and/or fat composition containing the XXX-type triglyceride as long as the effects of the present invention are not impaired. The other triglycerides include, for example, a X2Y-type triglyceride having a fatty acid residue Y in place of one of the fatty acid residues X of the XXX-type triglyceride and a XY2-type triglyceride having fatty acid residues Y in place of two of the fatty acid residues X of the XXX-type triglyceride.

When the total mass of the XXX-type triglyceride is set to 100% by mass, the amount of the other triglycerides is, for example, 0 to 100% by mass, preferably 0 to 70% by mass, and more preferably 1 to 40% by mass.

In addition, as the oil and/or fat composition of the present invention, it is possible to use one obtained by hydrogenation, transesterification, or separation of a triglyceride composition of natural origin instead of directly synthesizing the XXX-type triglyceride. The triglyceride composition or natural origin includes, for example, rapeseed oil, soybean oil, sunflower oil, high oleic sunflower oil, safflower oil, palm stearin, and mixtures thereof. In particular, hardened oil, partially hardened oil, and extremely hardened oil of these triglyceride compositions of natural origin are preferable. Hard palm stearin, high oleic extremely hardened sunflower oil, extremely hardened rapeseed oil, and extremely hardened soybean oil are further preferable.

Moreover, the oil and/or fat composition of the present invention includes a triglyceride composition or a synthetic oil and/or fat commercially available. For example, the triglyceride composition includes hard palm stearin (manufactured by manufactured by The Nisshin OilliO Group, Ltd.), extremely hardened rapeseed oil (manufactured by Yokozeki Oil & Fat Industries Co., Ltd.), and extremely hardened soybean oil (manufactured by Yokozeki Oil & Fat Industries Co., Ltd.). In addition, the synthetic oil and/or fat includes tripalmitin (manufactured by Tokyo Chemical Industry Co., Ltd.), tristearin (manufactured by Sigma-Aldrich Corporation), tristearin (manufactured by Tokyo Chemical Industry Co., Ltd.), triarachidin (manufactured by Tokyo Chemical Industry Co., Ltd.), and tribehenin (manufactured by Tokyo Chemical Industry Co., Ltd.). In addition to the above, extremely hardened palm oil can be used as a dilution component for triglyceride because of the small content of the XXX-type triglyceride.

<Other Components>

In addition to the triglycerides described above, the oil and/or fat composition may optionally contain other components such as a partial glyceride, a fatty acid, an antioxidant, an emulsifier, and a solvent such as water. The amount of the other components can be any amount as long as the effects of the present invention are not impaired and is, for example, 0 to 5% by mass, preferably 0 to 2% by mass, and more preferably 0 to 1% by mass when the total mass of the XXX-type triglyceride is set to 100% by mass.

If multiple components are contained, the oil and/or fat compositions described above may optionally be mixed. Although any known mixing method may be used as long as a homogeneous reaction substrate is obtained, the mixing can be performed with, for example, a paddle mixer, an agi homo mixer, a disper mixer, and the like.

Regarding the mixing, the mixing may be performed under heating as necessary. The heating is preferably the same as the heating temperature in step (b) to be described later, and is performed at, for example, 50 to 120° C., preferably 60 to 100° C., more preferably 70 to 90° C., and further preferably 80° C.

(b) Step of Obtaining Above-Described Oil and/or Fat Composition in Molten State Before above-described (d) step, the oil and/or fat composition prepared in step (a) described above is then cooled without heating if in the molten state at the time of preparation. However, if not in the molten state when prepared, the oil and/or fat composition is optionally heated to melt the triglycerides contained in the oil and/or fat composition. As a result, the oil and/or fat composition in the molten state is obtained.

Here, it is appropriate that the heating of the oil and/or fat composition is performed at a temperature equal to or more than the melting points of the triglycerides contained in the oil and/or fat composition described above, particularly at a temperature which makes it possible to melt the XXX-type triglyceride, for example 70 to 200° C., preferably 75 to 150° C., and more preferably 80 to 100° C. In addition, it is appropriate that the heating is continued for 0.1 to 3 hours, preferably 0.3 to 2 hours, and more preferably 0.5 to 1 hour, for example.

In addition, the liquid oil and/or fat composition in the molten state being an embodiment of the powderizing agent of the present invention is produced by step (a) or (b). The powdered oil and/or fat composition in the solid state being another embodiment of the powderizing agent of the present invention is further produced by step (d) below. Note that for the purpose of producing the powder oil and/or fat composition, it is necessary to perform cooling at the cooling temperature described below.

(d) Step of Obtaining Powder Oil and/or Fat Composition by Cooling Oil and/or Fat Composition in Molten State The oil and/or fat composition in the molten state prepared in step (a) or (b) described above is further cooled and solidified to form a powder oil and/or fat composition containing the β-type oil and/or fat and having a plate-shaped particle shape.

Here, for the purpose of "cooling and solidifying the oil and/or fat composition in the molten state," it is necessary to keep the oil and/or fat composition in the molten state at a temperature lower than the melting point of the β-type oil and/or fat of the oil and/or fat component contained in the oil and/or fat composition as the upper limit value of the cooling temperature. Consider the case of a XXX-type triglyceride having three stearic acid residues each with 18 carbon atoms, for example. Since the melting point of the β-type oil and/or fat is 74° C. (Table 1), the "temperature lower than the melting point of the β-type oil and/or fat of the oil and/or fat component contained in the oil and/or fat composition" is a temperature lower by 1 to 30° C. than the melting point (specifically 44 to 73° C.), preferably a temperature lower by 1 to 20° C. than the melting point (specifically 54 to 73° C.), more preferably a temperature lower by 1 to 15° C. than the melting point (specifically 59 to 73° C.), and particularly preferably a temperature lower by 1° C., 2° C., 3° C., 4° C., 5° C., 6° C., 7° C., 8° C., 9° C., or 10° C.

More preferably, it is appropriate that the lower limit value of the cooling temperature is kept equal to or higher than the cooling temperature obtained from the following formula in order to obtain the β-type oil and/or fat.

cooling temperature (° C.)=number of carbon atoms x×6.6-68

(in the formula, the number of carbon atoms x is the number of carbon atoms x of the XXX-type triglyceride contained in the oil and/or fat composition)

The cooling temperature is set as above or higher because it is necessary to set the cooling temperature to a temperature at which the α-type oil and/or fat and the β'-type oil and/or fat other than the β-type oil and/or fat do not crystallize in the crystallization of the oil and/or fat in order to obtain the β-type oil and/or fat containing the XXX-type triglyceride. Since the cooling temperature depends mainly on the size of the molecule of the XXX-type triglyceride, it can be understood that there is a certain correlation between the number of carbon atoms x and the lower limit value of the optimum cooling temperature.

Consider the case where the XXX-type triglyceride contained in the oil and/or fat composition is a XXX-type triglyceride having three stearic acid residues each with 18 carbon atoms, for example. The lower limit value of the cooling temperature becomes 50.8° C. or more. Thus, in the case of a XXX-type triglyceride having three stearic acid residues each with 18 carbon atoms, the temperature of "cooling and solidifying the oil and/or fat composition in the molten state" is more preferably 50.8° C. or more and 72° C. or less.

In addition, if the XXX-type triglyceride is a mixture of two or more types, it is possible to determine the lower limit value prioritizing the cooling temperature with the smaller number of carbon atoms x. Consider the case where the XXX-type triglyceride contained in the oil and/or fat composition is a mixture of a XXX-type triglyceride having three palmitic acid residues each with 16 carbon atoms and a XXX-type triglyceride having three stearic acid residues each with 18 carbon atoms, for example. The lower limit value of the cooling temperature becomes 37.6° C. or more prioritizing the smaller number of carbon atoms 16.

As another embodiment, it is appropriate that the lower limit value of the cooling temperature described above is a temperature equal to or higher than the melting point of the α-type oil and/or fat corresponding to the β-type oil and/or fat of the oil and/or fat composition containing the XXX-type triglyceride. Consider the case where the XXX-type triglyceride contained in the oil and/or fat composition is a XXX-type triglyceride having three stearic acid residues each with 18 carbon atoms, for example. Since the melting point of the α-type oil and/or fat of the XXX-type triglyceride having the three stearic acid residues is 55° C. (Table 1), the temperature of "cooling and solidifying the oil and/or fat composition in the molten state" in that case is preferably 55° C. or more and 72° C. or less.

As a still another embodiment, if x is 10 to 12, for example, the cooling of the oil and/or fat composition in the molten state is performed such that the final temperature reaches a temperature of preferably −2 to 46° C., more preferably 12 to 44° C., and further preferably 14 to 42° C. For example, the final temperature in the cooling is preferably 24 to 56° C., more preferably 32 to 54° C., and further preferably 40 to 52° C. if x is 13 or 14, preferably 36 to 66° C., more preferably 44 to 64° C., and further preferably 52 to 62° C. if x is 15 or 16, preferably 50 to 72° C., more preferably 54 to 70° C., and further preferably 58 to 68° C. if x is 17 or 18, preferably 62 to 80° C., more preferably 66 to 78° C., and further preferably 70 to 77° C. if x is 19 or 20, and preferably 66 to 84° C., more preferably 70 to 82° C., and further preferably 74 to 80° C. if x is 21 or 22. It is appropriate to allow the oil and/or fat composition to stand at the final temperature described above for preferably 2 hours or more, more preferably 4 hours or more, and further preferably 6 hours or more, and preferably 2 days or less, more preferably 24 hours or less, and further preferably 12 hours or less, for example.

(c) Step of Promoting Generation of Powder

As (c) an optional step for promoting the generation of powder before step (d) and between step (a) or (b) and (d) described above, one may further perform the treatment of a seeding process (c1), a tempering process (c2), and/or (c3) a pre-cooling process on the oil and/or fat composition in the molten state to be used in step (d). These optional steps (c1) to (c3) may be performed singly or in combination of two or more steps. Here, between step (a) or (b) and step (d) has a meaning which includes within step (a) or (b) and after step (a) or (b), and before step (d) and within step (d).

The seeding process (c1) and the tempering process (c2) are each a method of promoting the generation of powder in the production of the powder oil and/or fat composition of the present invention, which treats the oil and/or fat composition in the molten state before cooling to the final temperature in order to more reliably powderize the oil and/or fat composition in the molten state.

Here, the seeding process (c1) is a method of promoting powderization by adding a small amount of a component being a core (seed) of powder in the cooling of the oil and/or fat composition in the molten state. To be more specific, for example, together with the oil and/or fat composition in the molten state obtained in step (b), an oil and/or fat powder which contains a XXX-type triglyceride having carbon atoms equal to those of the XXX-type triglyceride in the oil and/or fat composition at preferably 80% by mass or more and more preferably 90% by mass or more, is prepared as a core (seed) component. The method promotes the powderization of the oil and/or fat composition by adding this oil and/or fat powder being the core at 0.1 to 1 part by mass and preferably 0.2 to 0.8 parts by relative to 100 parts by mass of the oil and/or fat composition in the molten state when, in the cooling of the oil and/or fat composition in the molten state, the temperature of the oil and/or fat composition reaches a temperature of the final cooling temperature ±0 to +10° C. and preferably +5 to +10° C., for example.

In addition, the tempering process (c2) is a method of promoting the powderization of the oil and/or fat composition by, before allowing the oil and/or fat composition to stand at the final cooling temperature in the cooling of the oil and/or fat composition in the molten state, once performing cooling at a temperature lower than the cooling temperature of step (d), for example a temperature lower by 5 to 20° C., a temperature lower by preferably 7 to 15° C., and a temperature lower by more preferably about 10° C. for preferably 10 to 120 minutes and more preferably about 30 to 90 minutes.

Moreover, the pre-cooling process (c3) is a method of, before cooling in step (d), once cooling the oil and/or fat composition in the molten state obtained in step (a) or (b) described above at a temperature between the temperature at which the oil and/or fat composition containing the XXX-type triglyceride described above is prepared and the cooling temperature at the time of cooling the oil and/or fat composition, in other words, a method of once pre-cooling the oil and/or fat composition in the molten state obtained in step (a) or (b) described above at a temperature lower than the temperature of the molten state of step (a) or (b) and at a temperature higher than the cooling temperature of step (d). Following (c3) the pre-cooling process, cooling is performed at the cooling temperature at the time of cooling the oil and/or fat composition step (d). The temperature higher than the cooling temperature of step (d) can be, for example, a temperature higher by 2 to 40° C., a temperature higher by preferably 3 to 30° C., a temperature higher by more preferably 4 to 30° C., and a temperature higher by further preferably about 5 to 10° C. than the cooling temperature of step (d). The lower the temperature for pre-cooling, the shorter the main cooling time at the cooling temperature of step (d) can be. To sum up, unlike the seeding process and the tempering process, the pre-cooling process is a method which can promote the powderization of the oil and/or fat composition by simply lowering step by step the cooling temperature, and has a great advantage in the case of industrial production.

(e) Step of Obtaining Powder Oil and/or Fat Composition by Pulverizing Solid.

The above step of obtaining the powder oil and/or fat composition by cooling of step (d) may be, more specifically, performed by step (e) of obtaining the powder oil and/or fat composition by pulverizing a solid obtained by cooling of step (d).

To explain the details, the oil and/or fat composition is first melted to obtain the oil and/or fat composition in the molten state, followed by cooling to form a solid having voids with an increased volume larger than the oil and/or fat composition in the molten state. The oil and/or fat composition formed into a solid having voids can easily be pulverized by applying a weak impact thereto. The solid easily collapses into a powder form.

Here, although the means of applying a weak impact is not particularly limited, a method of applying weak vibration (impact) for pulverization (loosening) by, for example, shaking or sieving is preferable because of its simplicity.

Note that the solid may be pulverized by known pulverization processing means. Examples of such pulverization processing means include a hammermill, a cutter mill, and the like.

<Optional Component in Oil and/or Fat Composition>

It is preferable that the oil and/or fat composition used in the present invention (which has two embodiments of a liquid form and a powder form) is essentially composed only of oil and/or fat. Here, the oil and/or fat is essentially composed only of triglycerides. In addition, "essentially" means that the components other than the oil and/or fat contained in the oil and/or fat composition or the components other than the triglycerides contained in the oil and/or fat are, for example, 0 to 15% by mass, preferably 0 to 10% by mass, and more preferably 0 to 5% by mass when the oil and/or fat composition or the oil and/or fat is set to 100% by mass.

<Powderizing Agent>

The powderizing agent of the present invention contains the above-described oil and/or fat composition (which has two embodiments of a liquid form and a powder form) as an essential component.

The powdered oil and/or fat composition used as the powderizing agent of the present invention is preferably a powder body having an average particle diameter of 10 to 1000 μm, more preferably a powder body having an average particle diameter of 20 to 200 μm, and further preferably a powder body of 50 to 100 μm. If a powder body having the average particle diameter described above is used, it is possible to obtain a smooth powder composition having a uniform distribution of the liquid component and the powderizing agent. Note that the average particle diameter mentioned here is a value measured by laser diffraction scattering method (ISO 133201 and ISO 9276-1).

In addition, a powder body having the average particle diameter described above can be produced by using known pulverization means, for example spraying or a pulverizer, which is generally used for production of oils and/or fats.

It is preferable that the powderizing agent of the present invention is composed only of the oil and/or fat composition.

Note that the powderizing agent of the present invention may contain an optional component in addition to the oil and/or fat composition described above as long as the functions as the powderizing agent are not impaired. The optional component mentioned here refers to a component other than the liquid component (powderization target) to be described later. The optional component includes an emulsifier, skim milk powder, whole milk powder, cocoa powder, sugar, dextrin, and the like.

The amount of the optional component blended is, for example, 0 to 70% by mass, preferably 0 to 65% by mass, and more preferably 0 to 30% by mass when the total mass of the powderizing agent is set to 100% by mass.

Preferably, 90% by mass or more of the optional component is a powder body having an average particle diameter of 1000 μm or less and more preferably a powder body having an average particle diameter of 500 μm or less from the viewpoint that it is possible to obtain a smooth powder composition having a uniform distribution of the liquid component and the powderizing agent. Note that the average particle diameter mentioned here is a value measured by laser diffraction scattering method (ISO 133201 and ISO 9276-1).

Next, a description is provided for a method of powderizing the liquid component by using the powderizing agent of the present invention (in other words, a method of producing a powder composition by powderizing the liquid component).

<Liquid Component>

The liquid component refers to a liquid which contains the functional materials contained in the product to be described later.

In addition, the liquid component refers to a component which is a liquid at normal temperature (20° C.).

Regarding the functional materials, it is possible to use ones capable of adding a certain function to the product without particular limitation.

In addition, the functional materials may be a substance which adds a primary function of the product (for example, active components in medicinal drugs or functional foods) or a substance which adds a secondary function of the product (for example, dyes and flavors in food).

The functional material may be used singly or in appropriate combination of two or more types.

The functional material can be divided into hydrophobic substances and hydrophilic substances.

<Hydrophobic Substance>

Regarding the hydrophobic substances, it is possible to use ones blended in the product described later as functional materials without particular limitation. Specific examples include a flavor, a dye, a vitamin, a lipid, a protein (hydrophobic peptide), and the like. Among these, the present invention is preferably applicable to a flavor, a dye, a vitamin, and lecithin.

Regarding the flavor, it is possible to use, for example, ones blended in foods and/or beverages, cosmetics, quasi drugs, pharmaceutical drugs, and the like without particular limitation. Specific examples include menthol, cocoas (powder, extract, and the like), esters (for example, isoamyl acetate, linalyl acetate, isoamyl propionate, linalyl butyrate, and the like), natural essential oils (examples of plant essential oil are vanilla extract, spearmint, peppermint, cassia, jasmine, and the like; examples of animal essential oil are musk, ambergris, civet, castoreum, and the like), aromatic chemicals (for example, anethole, limonene, linalool, eugenol, vanillin, and the like), and oily seasonings (roasted shrimp oil, onion oil, and the like), and more specifically include roasted garlic oil, limonene, vanillin, roasted shrimp oil, onion oil, and the like.

Regarding the dye, it is possible to use, for example, ones blended in foods and/or beverages, cosmetics, quasi drugs, pharmaceutical drugs, and the like without particular limitation. Specific examples include an orange dye, a yellow dye, a magenta dye, a cyan dye, and the like.

Regarding the vitamin, it is possible to use, for example, ones blended in foods and/or beverages, cosmetics, quasi drugs, pharmaceutical drugs, and the like without particular limitation. Specific examples include vitamin E, vitamin A, vitamin D, vitamin K, and the like.

Regarding the lipid, it is possible to use, for example, ones blended in foods and/or beverages, cosmetics, quasi drugs, pharmaceutical drugs, and the like without particular limitation. Specific examples include a triglyceride, a fatty acid, a phospholipid (for example, lecithin, lysolecithin, phosphatidic acid, lysophosphatidic acid, and the like), triethylhexanoin, and the like.

The protein includes a hydrophobic peptide, and the peptide is a series of 3 or more amino acids. Hydrophobicity means a low solubility to water, and hydrophobicity is here defined to be a solubility of less than 1 μg per 1 ml of water.

The hydrophobic substance may be used singly or in appropriate combination of two or more types for use as a mixture.

The liquid component may be a solution of the hydrophobic substances. Regarding the solvent constituting the solution, it is possible to use ones capable of dissolving the hydrophobic substances without particular limitation. Specific examples include a liquid oil, an alcohol, an organic solvent, and the like. Regarding the solution of the hydrophobic substances, it is preferable that the solution itself is hydrophobic.

Regarding the liquid oil, it is possible to use, for example, ones blended in foods and/or beverages, cosmetics, quasi drugs, pharmaceutical drugs, and the like without particular limitation. Specific examples include edible oil and/or fats such as rapeseed oil, olive oil, rice bran oil, sesame oil, cottonseed oil, peanut oil, corn oil, soybean oil, sunflower oil, safflower oil, grape seed oil, macadamia nut oil, hazelnut oil, pumpkin seed oil, walnut oil, tea seed oil, tea oil, MCT oil (note that the XXX-type triglyceride constituting the powderizing agent described above is excluded), and MLCT oil.

Regarding the alcohol, it is possible to use, for example, ones blended in foods and/or beverages, cosmetics, quasi drugs, pharmaceutical drugs, and the like without particular limitation. Specific examples include, for example, lower alcohols such as methyl alcohol, ethyl alcohol, n-propyl alcohol, isopropyl alcohol, or butyl alcohol.

Regarding the organic solvent, it is possible to use, for example, ones blended in foods and/or beverages, cosmetics, quasi drugs, pharmaceutical drugs, and the like without particular limitation. Specific examples include ethyl acetate, butyl acetate, diethyl ether, methyl ether, methyl isobutyl ketone, hexane, acetone, chloroform, or the like.

The solvent may be used singly or in appropriate combination of two or more types for use as a mixture.

Although no particular limitation is imposed, the content of the hydrophobic substances in the solution is, for example, 1 to 99% by mass, preferably 5 to 80% by mass, and further preferably 10 to 60% by mass relative to the total mass of the solution.

The liquid component may be an emulsion of the hydrophobic substances. Regarding the dispersion medium constituting the emulsion, it is possible to use ones capable of dispersing the hydrophobic substances without particular limitation. Specific examples include water, glycerin, a sugar alcohol, a liquid oil, and the like, preferably water, glycerin, and a liquid oil, and more preferably water and glycerin.

The dispersion medium may be used singly or in appropriate combination of two or more types.

The emulsion may contain an emulsifier. Regarding the emulsifier, it is possible to use ones capable of dispersing the hydrophobic substances without particular limitation. Specific examples include glycerin fatty acid ester, propylene glycol fatty acid ester, sucrose fatty acid ester, polyglycerin fatty acid ester, sorbitan fatty acid ester, a fatty acid salt, alkyl sulfuric acid ester, an alkyl amine salt, a quaternary ammonium salt, alkyl betaine, lecithin, Quillaia extract, gum arabic, gum tragacanth, guar gum, karaya gum, xanthan gum, pectin, pullulan, cyclodextrin, alginic acid and salts thereof, carrageenan, gelatin, casein, starch, derivatives of starch, and the like, preferably glycerin fatty acid ester, propylene glycol fatty acid ester, sucrose fatty acid ester, polyglycerin fatty acid ester, lecithin, and sorbitan fatty acid ester, and more preferably glycerin fatty acid ester, sucrose fatty acid ester, polyglycerin fatty acid ester, and lecithin.

The emulsifier may be used singly or in appropriate combination of two or more types.

Although no particular limitation is imposed, the content of the hydrophobic substances in the emulsion is, for example, 1 to 99% by mass, preferably 5 to 80% by mass, and further preferably 10 to 60% by mass relative to the total mass of the solution.

Note that the liquid component may be the molten hydrophobic substances themselves (a melt). In this case, the liquid component is made up only of the hydrophobic substances. The hydrophobic substances usable as a melt include, for example, vitamin E, limonene, vanillin, and the like.

<Hydrophilic Substance>

Regarding the hydrophilic substances, it is possible to use ones blended in the product described later as functional materials without particular limitation. Specific examples include a flavor, a dye, a vitamin, an available carbohydrate, a protein (hydrophilic peptide), a nucleic acid, and the like. Among these, the present invention is preferably applicable to a flavor, a dye, and a vitamin.

Regarding the flavor, it is possible to use, for example, ones blended in foods and/or beverages, cosmetics, quasi drugs, pharmaceutical drugs, and the like without particular limitation. Specific examples include aqueous flavors (for example, shrimp flavor), aqueous seasonings (for example, shrimp flavor), natural plant flavors (for example, liquorice, Saint John's bread, prunus salicina extract, peach extract, and the like), acids (for example, malic acid, tartaric acid, citric acid, butyric acid, and the like), and the like.

Regarding the dye, it is possible to use, for example, ones blended in foods and/or beverages, cosmetics, quasi drugs, pharmaceutical drugs, and the like without particular limitation. Specific examples include an azine-based dye, an acridine-based dye, a triphenylmethane-based dye, a xanthene-based dye, a porphyrin-based dye, a cyanine-based dye, a phthalocyanine-based dye, a styryl-based dye, a pyrylium-based dye, an azo-based dye, a quinone-based dye, a tetracycline-based dye, a flavone-based dye, a polyene-based dye, a BODIPY (registered trademark)-based dye, an indigoid-based dye, and the like.

Regarding the vitamin, it is possible to use, for example, ones blended in foods and/or beverages, cosmetics, quasi drugs, pharmaceutical drugs, and the like without particular limitation. Specific examples include vitamins B1, B2, and B6, nicotinic acid, pantothenic acid, vitamin B12, vitamin C, and the like.

Regarding the available carbohydrate, it is possible to use, for example, ones blended in foods and/or beverages, cosmetics, quasi drugs, pharmaceutical drugs, and the like without particular limitation. Specific examples include polysaccharides such as starch, dextrin, α-cyclodextrin, dextran, pullulan, gum arabic, tragacanth, and agar, monosaccharides such as glucose, fructose, and galactose, and oligosaccharides.

The protein includes a hydrophilic peptide, and the peptide is a series of 3 or more amino acids. Hydrophilicity means a high solubility to water, and hydrophilicity is here defined to be a solubility of 1 μg or more per 1 ml of water.

The nucleic acid includes deoxyribonucleic acid (DNA), ribonucleic acid (RNA), DNA-RNA hybrid, an oligonucleotide, a polynucleotide, an aptamer, a peptide nucleic acid (PNA), and the like.

The hydrophilic substances may be used singly or in appropriate combination of two or more types for use as a mixture.

The liquid component may be a solution of the hydrophilic substances. Regarding the solvent constituting the solution, it is possible to use ones capable of dissolving the hydrophilic substances without particular limitation. Specific examples include water, an alcohol, an organic solvent, and the like, preferably water and an alcohol, and more preferably water. Regarding the solution of the hydrophilic substances, it is preferable that the solution itself is hydrophilic.

Regarding the alcohol, it is possible to use, for example, ones blended in foods and/or beverages, cosmetics, quasi drugs, pharmaceutical drugs, and the like without particular limitation. Specific examples include, for example, monovalent lower alcohols such as ethanol, n-propanol, isopropanol, and n-butanol; divalent alcohols such as 1,3-butylene glycol, ethylene glycol, and propylene glycol; polyalkylene glycols such as polyethylene glycol, dipropylene glycol, and polypropylene glycol; and polyvalent alcohols such as glycerin, diglycerin, trimethylolpropane, pentaerythritol, and sorbitol.

Regarding the organic solvent, it is possible to use, for example, ones blended in foods and/or beverages, cosmetics, quasi drugs, pharmaceutical drugs, and the like without particular limitation. Specific examples include glycols, esters, ethers, ketones, and the like. The glycols include, for example, ethylene glycol and propylene glycol. The esters include esters of the alcohols and glycols described above with formic acid, acetic acid, propionic acid, and the like, specifically methyl formate, ethyl formate, butyl formate, methyl acetate, ethyl acetate, butyl acetate, ethyl propionate, and the like. The ethers include alkyl ethers and the like of the alcohols and glycols described above, specifically dimethyl ether, diethyl ether, dibutyl ether, methyl ethyl ether, ethyl butyl ether, ethylene glycol monobutyl ether, ethylene glycol acetate monoethyl ether, propylene glycol monoethyl ether, and the like. The ketones include acetone, diethyl ketone, methyl ethyl ketone, acetophenone, and the like.

The solvent may be used singly or in appropriate combination of two or more types for use as a mixture.

Although no particular limitation is imposed, the content of the hydrophilic substances in the solution is, for example, 1 to 99% by mass, preferably 5 to 80% by mass, and further preferably 10 to 70% by mass relative to the total mass of the solution.

The liquid component may be an emulsion of the hydrophilic substances. Regarding the dispersion medium constituting the emulsion, it is possible to use ones capable of dispersing the hydrophilic substances without particular limitation. Specific examples include water, glycerin, a sugar alcohol, a liquid oil, and the like, preferably water, glycerin, and a liquid oil, and more preferably water and glycerin.

The dispersion medium may be used singly or in appropriate combination of two or more types.

The emulsion may contain an emulsifier. Regarding the emulsifier, it is possible to use ones capable of dispersing the hydrophilic substances without particular limitation. Specific examples include sucrose fatty acid ester, polyglycerin fatty acid ester, organic acid monoglycerin fatty acid ester, lysolecithin, and the like, preferably sucrose fatty acid ester, polyglycerin fatty acid ester, and organic acid monoglycerin fatty acid ester, and more preferably sucrose fatty acid ester and organic acid monoglycerin fatty acid ester.

The emulsifier may be used singly or in appropriate combination of two or more types.

Although no particular limitation is imposed, the content of the hydrophilic substances in the emulsion is, for example, 1 to 99% by mass, preferably 5 to 80% by mass, and further preferably 10 to 60% by mass relative to the total mass of the solution.

Note that the liquid component may be the molten hydrophilic substances themselves (a melt). In this case, the liquid component is made up only of the hydrophilic substances. The hydrophilic substances usable as a melt include, for example, water, a sugar alcohol (for example, erythritol, maltitol, and the like), and the like.

In addition, the liquid component may be ones containing hydrophobic substances and/or hydrophilic substances, for example liquid form food. Specific examples of the liquid form food include cow's milk, wine, fruit juice, stock, yogurt, and the like, preferably cow's milk and fruit juice. Note that the "fruit juice" described above includes 100% juices such as orange juice. In addition, regarding the liquid form food, it is preferable that the food itself is hydrophilic.

Note that the liquid component includes solutions and emulsions containing water as a functional material, and water itself (a functional material only).

<Method of Powderizing Liquid Component (Method of Producing Powder Composition)>

The present invention powderizes the liquid component by mixing the powderizing agent and the liquid component in the mixing step, and thereby produces a powder composition containing the powderized liquid component (hereinafter also referred to as the "powder composition"). The powderizing agent used in the production of the powder composition may be in the molten state (liquid form) or in the solid state (powder form). In the case of using one in the molten state, the cooling step to be described later is necessary. Note that if a powderizing agent in the solid state (powder form) is used, it is possible to skip this cooling step.

Hereinafter, a description is provided for a method of producing the powder composition using the powderizing agent.

<Mixing Step>

The powderizing agent to be subjected to the mixing step may be in the molten state (liquid form) or in the solid state (powder form), but is preferably used in the molten state. Use in the molten state makes it possible for the powderizing agent and the liquid component to mix well with each other, making it possible to obtain a more homogeneous powder composition.

No particular limitation is imposed on the mass ratio between the powderizing agent and the liquid component in the mixing step (powderizing agent:liquid component).

In addition, the amount of the liquid component used may be, for example, 0.1 to 30% by mass, preferably 0.3 to 25% by mass, and more preferably 0.5 to 20% by mass relative to the total mass of the powder composition (final product). If the amount used is as described above, it is possible to more sufficiently powderize the liquid component.

Although any known mixing means may be used as long as a homogeneous mixture is obtained, the mixing can be performed with, for example, a paddle mixer, an agi homo mixer, a disper mixer, and the like.

Regarding the mixing, the mixing may be performed under heating as necessary. In the case of using the powderizing agent in the molten state, the mixing temperature is, for example, 5 to 120° C., preferably 50 to 100° C., and more preferably 55 to 90° C. In the case of using the powderizing agent in the powder form, the mixing temperature is, for example, 5 to 40° C., preferably 10 to 30° C., and more preferably 15 to 25° C. Note that in the case of powderizing a particularly heat sensitive liquid component (for example, flavor, dye, vitamin, and the like), the mixing temperature is set to a temperature which does not cause decomposition or modification of the liquid component.

Although no particular limitation is imposed on the mixing time, the powderizing agent and the liquid component may be mixed until a sufficiently uniform mixture is formed, and the mixing time is, for example, 5 to 60 minutes, preferably 10 to 50 minutes, and more preferably 20 to 40 minutes.

<Cooling Step>

There is a case where the mixture of the powderizing agent and the liquid component is subsequently subjected to the cooling step for powderization. In particular, if an oil and/or fat composition in the molten state (liquid form) is used as the powderizing agent described above, the mixture is subjected to the cooling step for powderization because the state of the mixture is the liquid form. Note that if an oil and/or fat composition in the solid state (powder form) is used as the powderizing agent described above, the mixture is usually in the solid state (powder form), and the cooling step is an optional step performed as necessary.

The cooling step is the same as the cooling step used when obtaining the powder oil and/or fat composition explained in the paragraphs above. For example, the cooling step is performed on the oil and/or fat composition in the molten state at a temperature which is lower than the melting point of the β-type oil and/or fat of the oil and/or fat component contained in the oil and/or fat composition and at a temperature which is equal to or higher than the cooling temperature obtained from the following formula:

cooling temperature (° C.)=number of carbon atoms $x \times 6.6 - 68$.

Cooling in such a temperature range makes it possible to efficiently produce the β-type oil and/or fat, followed by formation of fine crystal. Thus, it is possible to easily obtain a powder composition.

In addition, if x is 10 to 12, for example, the cooling of the mixture is performed such that the final temperature reaches a temperature of preferably −2 to 46° C., more preferably 12 to 44° C., and further preferably 14 to 42° C. For example, the final temperature in the cooling is preferably 24 to 56° C., more preferably 32 to 54° C., and further preferably 40 to 52° C. if x is 13 or 14, preferably 36 to 66° C., more preferably 44 to 64° C., and further preferably 52 to 62° C. if x is 15 or 16, preferably 50 to 72° C., more preferably 54 to 70° C., and further preferably 58 to 68° C. if x is 17 or 18, preferably 62 to 80° C., more preferably 66 to 78° C., and further preferably 70 to 77° C. if x is 19 or 20, and preferably 66 to 84° C., more preferably 70 to 82° C., and further preferably 74 to 80° C. if x is 21 or 22. It is appropriate to allow the mixture to stand at the final temperature described above for preferably 2 hours or more, more preferably 4 hours or more, and further preferably 6 hours or more, and preferably 2 days or less, more preferably 24 hours or less, and further preferably 12 hours or less, for example.

<Step of Promoting Powderization (Seeding Method, Tempering Method, and/or Pre-Cooling Method)>

For the purpose of promoting the powderization in the cooling step, the seeding process, the tempering process, and/or pre-cooling process may be performed as an optional step for promoting powderization between the mixing step and the cooling step.

Here, "between the mixing step and the cooling step" has a meaning which includes within the mixing step and after the mixing step, and before the cooling step and within the cooling step.

As the seeding process, it is possible to use the seeding process (c1) described above in relation to the production of the powder oil and/or fat composition constituting the powderizing agent.

As the tempering process, it is possible to use the tempering process (c2) described above in relation to the production of the powder oil and/or fat composition constituting the powderizing agent.

As the pre-cooling process, it is possible to use the pre-cooling process (c3) described above in relation to the production of the powder oil and/or fat composition constituting the powderizing agent.

<Drying Step>

Although the product after the mixing step or the cooling step is formed into powder without being subjected to a particular step (for example, by adding a weak impact), a drying step may be performed as an optional step for more promoting powderization. The drying step is particularly useful if the liquid component is a solution or an emulsion of the functional materials and the content of the solvent of the solution or of the dispersion medium of the emulsion is high (for example, the content of the solvent or the dispersion medium is 50 to 90% by mass relative to the total mass of the liquid component).

The temperature employed in the drying step may be a temperature which can evaporate the solvent or the dispersion medium described above and is, for example, 10 to 80° C., preferably 20 to 60° C., and more preferably 25 to 50° C.

Note that the production method of the present invention does not use a drying step which employs a temperature that could cause decomposition or modification of the liquid component. The drying step is performed at a temperature which does not cause decomposition or modification of the liquid component in the case of powderizing a particularly heat sensitive liquid component (for example, flavor, dye, vitamin, and the like).

Note that if the seeding, the tempering process, and/or the pre-cooling process are performed, the drying step is preferably performed after the seeding process, the tempering process, and/or the pre-cooling process.

<Pulverization Step>

The product after the mixing step or the cooling step is a solid having voids with an increased volume. For this reason, without a particular step (for example, by applying a weak impact), the solid easily collapses, is pulverized, and formed into a powder form. Thus, although active pulverization means is not necessary, a pulverization step may be performed as an optional step.

The pulverization means may be strong machine pulverization means using spraying or a pulverizer (a mill and the like), but means of applying a weak impact (vibration) is sufficient. Although the means of applying a weak impact (vibration) is not particularly limited, means of applying weak vibration (impact) for pulverization (loosening) by, for example, shaking or sieving is preferable because of its simplicity.

Although the present invention does not intend to be bound by a particular theory, use of the powderizing agent of the present invention makes it possible to easily powderize the liquid component presumably because of the characteristics of the oil and/or fat composition contained in the powderizing agent. To be more specific, we consider as follows. When adjusted to appropriate temperature conditions, the XXX-type triglyceride crystallizes in a very hollowly state (state where the volume has increased and voids have been formed). Here, the liquid component is taken in the voids to become a solid. Thus, powderization is achieved. It is considered that the liquid component is also taken in the voids by adding the powderizing agent in the powder form to the liquid component. The obtained solid has the form of an aggregate of the oil and/or fat composition having the liquid component taken therein, fragilely collapses by a weak impact, and is easily formed into powder.

<Characteristics of Powder Composition>

The powder composition obtained by applying the powderizing agent of the present invention to the liquid component is a solid in the form of powder at room temperature (20° C.)

The loose bulk density of the powder composition is 0.05 to 0.6 g/cm$^3$, preferably 0.1 to 0.5 g/cm$^3$, more preferably 0.15 to 0.45 g/cm$^3$, and further preferably 0.2 to 0.4 g/cm$^3$.

Here, the "loose bulk density" is the bulk density of a powder body which has freely fallen. The measurement of the loose bulk density (g/cm$^3$) can be obtained as follow. For example, a graduated cylinder having an inner diameter of 15 mm×25 mL is loosely filled with an appropriate amount of the powder composition allowed to fall from about 2 cm above the upper open end of the graduated cylinder. Then, the packed mass (g) is measured and the volume (mL) is read. Finally, the mass (g) of the powder composition per mL is calculated. In addition, the loose bulk density can be calculated by using a bulk specific gravity measurement apparatus of Kuramochi Kagakukikai Seisakusho and using a bulk specific gravity measured based on JIS K-6720 (or ISO 1060-1 and -2). To be more specific, 120 mL of sample is allowed to fall onto a receiver (100 mL cylindrical container having an inner diameter of 40 mm×height 85 mm) from a position higher by 38 mm than the upper open end of the receiver. A portion of the sample sticking out of the receiver is removed, and the mass (A g) of the sample corresponding to the internal volume of the receiver (100 mL) is weighed. The loose bulk density can be obtained by the following formula.

loose bulk density (g/mL)=$A$ (g)/100 (mL)

It is preferable that the measurement is performed three times and the average value thereof is taken.

In addition, the powder composition has the form of, for example, a spherical crystal or a plate-shaped crystal, and usually has the form of a plate-shaped crystal. In addition, the powder composition has an average particle diameter of, for example, 10 to 400 μm, preferably 20 to 300 μm, more preferably 30 to 250 μm, and especially preferably 50 to 200 μm. Here, the average particle diameter can be obtained with a particle size distribution measurement apparatus (for example, Microtrac MT 3300 ExII manufactured by Nikkiso Co., Ltd.) based on the laser diffraction scattering method (ISO 133201 and ISO 9276-1).

The expansion ratio of the powder composition is, for example, 1.0 to 6.0, preferably 1.2 to 5.5, and more preferably 1.5 to 5.0. An expansion ratio of 2.0 or more is preferable from the viewpoint that, for example, it is easy to take the liquid component in for powderization because a sufficient amount of void is contained in the powder composition. Here, the expansion ratio is represented as a ratio of the height of the vertex of the powderized composition after powderization to the height of the melt of the liquid component and the powderizing agent before powderization.

<Use of Powder Composition>

The powder composition obtained by applying the powderizing agent of the present invention to the liquid component can be used in various products without particular limitation depending on the functions provided by the functional materials contained in the powderized liquid component.

Specific examples of the products include, for example, foods and/or beverages, cosmetics, quasi drug, pharmaceutical drugs, household goods, feeds, general goods, agricultural chemicals, industrial chemical products, and the like.

In addition, the powder composition itself may be used as a product (for example, powdered food) and may be used as a raw material or an intermediate of the above-described product.

<Foods and/or Beverages>

The present invention also relates to foods and/or beverages particularly containing the powder composition described above. The foods and/or beverages include, for example, luxury foods without particular limitation.

Regarding the luxury foods, it is possible to use ones which can be blended with the powder composition of the present invention without particular limitation. Examples include cooking materials, processed foods, cooked foods, and the like. Specific examples include oils and/or fats or processed oils and/or fats (for example, deep frying oil for business use or household use, stir frying oil, spray oil, baking tray oil, margarine, fat spread, shortening, flour paste, creams, powder oils and/or fats, emulsified oils and/or fats, and the like), instant foods (for example, instant noodles, cup noodles, instant soups and stews, and the like), retort foods and canned foods (for example, curry, soup, stews, pasta sauce, prepared Chinese foods, prepared donburi, and the like), functional foods (for example, high-calorie beverages, fluid diets, balanced nutrition foods, dietary supplements, food for specified health uses, and the like), wheat flour or starch foods (for example, bread, pastas such as macaroni and spaghetti, pizza pies, noodles, cake mixes, processed cooked rice, serials, and the like), confectionery and desserts (for example, caramel, candies, chewing gum, chocolate, cookies and biscuits, cakes, pies, snacks, crackers, wagashi, beika, mamegashi, jellies, pudding, and the like), basic seasonings (for example, soy sauce, miso, sauces, and the like), flavor enhancers (curry or roux for stew, tare sauces, dressings, mayonnaise-like seasoning, noodle soup base, soup base for nabemono, chili oil, mustard, karashi, wasabi, grated ginger, grated onion, prepared kimchi, demi-glace, white sauce, tomato sauce, and the like), dairy products (for example, milk, processed milk, yogurts, lactic acid bacteria beverages, cheeses, ice creams, powdered infant formula, creams, and the like), processed marine products (for example, canned marine products, fish ham or sausage, pastes of marine product, canned oil immersed fish, and the like), processed agricultural products (for example, peanut butter, jam, marmalade, chocolate cream, processed menma products, processed zha cai products, nerigoma, sesame paste, and the like), processed livestock products (for example, animal meat ham or sausage, canned animal meat, pastes, hamburg steak, meatballs, flavored canned animal meat, and the like), cooked or half cooked foods (for example, frozen foods, refrigerated foods, packed side dishes, side dishes for storefront sale, and the like). In addition, the foods and/or beverages containing the powder composition of the present invention may be foods and/or beverages used for non-humans, for example pet foods for pets and feeds for livestock.

Next, the effects of the present invention are described in detail using Examples, but the present invention is not limited to Examples.

EXAMPLES

Preparation of Powderizing Agent

The powderizing agents A and A' described below were prepared.

Powderizing Agent

Extremely hardened rapeseed oil commercially available (manufactured by Yokozeki Oil & Fat Industries Co., Ltd.) was used as the oil and/or fat composition.

When the total triglyceride content (content of the oil and/or fat component) was set to 100% by mass, the oil and/or fat composition was an oil and/or fat composition containing 79.1% by mass of the XXX-type triglyceride having fatty acid residues X, each with x (x=18) carbon atoms, at positions 1 to 3.

In addition, the melting point of this oil and/or fat composition was about 67° C. This oil and/or fat composition is transformed into the liquid state (liquid form) when heated and melted.

This oil and/or fat composition was used as the powderizing agent A described later.

Moreover, 25 g of this oil and/or fat composition was kept at 80° C. for 0.5 hours for complete melting, followed by cooling in a 55° C.-thermostatic chamber for 12 hours to form a solid having voids with an increased volume. After the crystallization was completed, cooling was performed to the room temperature (25° C.) state. The obtained solid was loosened to obtain a crystalline composition in the solid state (powder form) (loose bulk density: 0.2 g/cm$^3$, aspect ratio 1.6 (plate shape), average particle diameter 54 μm, X-ray diffraction measurement diffraction peak: 4.6 Å (peak characteristic of the β-type oil and/or fat), and peak intensity ratio: 0.89).

This oil and/or fat composition was used as the powderizing agent A' described later.

Loose Bulk Density

The loose bulk density was calculated by using a bulk specific gravity measurement apparatus of Kuramochi Kagakukikai Seisakusho and using a bulk specific gravity measured based on JIS K-6720 (or ISO 1060-1 and -2). To be more specific, 120 mL of sample was allowed to fall onto a receiver (100 mL cylindrical container having an inner diameter of 40 mm×height 85 mm) from a position higher by 38 mm than the upper open end of the receiver. Subsequently, a portion of the sample sticking out of the receiver was removed, and the mass (A g) of the sample corresponding to the internal volume of the receiver (100 mL) was weighed. The loose bulk density was obtained by the following formula.

loose bulk density (g/mL)=$A$ (g)/100 (mL)

The measurement was performed three times and the average value thereof was set to the measurement value.

Average Particle Diameter

The average particle diameter was measured with Microtrac MT 3300 ExII manufactured by Nikkiso Co., Ltd. based on the laser diffraction scattering method (ISO 133201 and ISO 9276-1).

Expansion Ratio

The expansion ratio was measured as a ratio of the height of the vertex after powderization to the height at the time of complete dissolution.

Examples 1 to 3 employed roasted garlic oil (hydrophobic flavor) as the liquid component.

Example 1

Into SV-110 (manufactured by Nichiden-Rika Glass Co., Ltd.), 9.9 g of the powderizing agent A and 0.1 g of roasted garlic oil (manufactured by Takata Koryo Co., Ltd.) (composition: 90% by mass of edible oil, 9.8% by mass of flavor, and 0.2% by mass of extracted vitamin E) (edible oil is the solvent of the flavor) were placed. These were kept at 80° C. for 0.5 hours and completely melt for mixing. Here, the amount of the liquid component used was 1% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder composition was obtained by loosening the obtained solid.

The characteristics of the obtained powder composition were as follows.

loose bulk density: 0.3 g/cm$^3$ average particle diameter: 58 μm expansion ratio: ×2.5

As illustrated in FIG. 1, the powder composition obtained in Example 1 was in the form of powder.

Example 2

Into SV-110 (manufactured by Nichiden-Rika Glass Co., Ltd.), 9.5 g of the powderizing agent A and 0.5 g of roasted garlic oil (manufactured by Takata Koryo Co., Ltd.) (composition: 90% by mass of edible oil, 9.8% by mass of flavor, and 0.2% by mass of extracted vitamin E) were placed. These were kept at 80° C. for 0.5 hours and completely melt for mixing. Here, the amount of the liquid component used was 5% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder composition was obtained by loosening the obtained solid.

The characteristics of the obtained powder composition were as follows.

loose bulk density: 0.3 g/cm$^3$ average particle diameter: 62 μm expansion ratio: ×2.4

As illustrated in FIG. 1, the powder composition obtained in Example 2 was in the form of powder.

Example 3

Into SV-110 (manufactured by Nichiden-Rika Glass Co., Ltd.), 9.0 g of the powderizing agent A and 1.0 g of roasted garlic oil (manufactured by Takata Koryo Co., Ltd.) (composition: 90% by mass of edible oil, 9.8% by mass of flavor, and 0.2% by mass of extracted vitamin E) were placed. These were kept at 80° C. for 0.5 hours and completely melt for mixing. Here, the amount of the liquid component used was 10% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder composition was obtained by loosening the obtained solid.

The characteristics of the obtained powder composition were as follows.
  loose bulk density: 0.3 g/cm³
  average particle diameter: 67 μm
  expansion ratio: ×1.9

As illustrated in FIG. 1, the powder composition obtained in Example 3 was in the form of powder.

Examples 4 to 6 employed shrimp flavor (hydrophilic flavor) as the liquid component.

Example 4

Into SV-110 (manufactured by Nichiden-Rika Glass Co., Ltd.), 9.9 g of the powderizing agent A and 0.1 g of shrimp flavor (manufactured by Takata Koryo Co., Ltd.) (composition: 50% by mass of ethanol, 30% by mass of purified water, 18% by mass of glycerin, and 2% by mass of flavor base) (ethanol, purified water, and glycerin are each the solvent of shrimp flavor) were placed. These were kept at 80° C. for 0.5 hours and completely melt for mixing. Here, the amount of the liquid component used was 1% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
  loose bulk density: 0.3 g/cm³
  average particle diameter: 60 μm
  expansion ratio: ×2.8

Figure 2:
FIG. 2 is a view illustrating powder compositions obtained in Examples 4 to 6.

As illustrated in FIG. 2, the powder composition obtained in Example 4 was in the form of powder.

Example 5

Into SV-110 (manufactured by Nichiden-Rika Glass Co., Ltd.), 9.5 g of the powderizing agent A and 0.5 g of shrimp flavor (manufactured by Takata Koryo Co., Ltd.) (composition: 50% by mass of ethanol, 30% by mass of purified water, 18% by mass of glycerin, and 2% by mass of flavor base) were placed. These were kept at 80° C. for 0.5 hours and completely melt for mixing. Here, the amount of the liquid component used was 5% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
  loose bulk density: 0.3 g/cm³
  average particle diameter: 64 μm
  expansion ratio: ×2.5

As illustrated in FIG. 2, the powder composition obtained in Example 5 was in the form of powder.

Example 6

Into SV-110 (manufactured by Nichiden-Rika Glass Co., Ltd.), 9.0 g of the powderizing agent A and 1.0 g of shrimp flavor (manufactured by Takata Koryo Co., Ltd.) (composition: 50% by mass of ethanol, 30% by mass of purified water, 18% by mass of glycerin, and 2% by mass of flavor base) were placed. These were kept at 80° C. for 0.5 hours and completely melt for mixing. Here, the amount of the liquid component used was 10% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
  loose bulk density: 0.3 g/cm³
  average particle diameter: 70 μm
  expansion ratio: ×2.2

As illustrated in FIG. 2, the powder composition obtained in Example 6 was in the form of powder.

Examples 7 to 9 employed vitamin E (hydrophobic vitamin) as the liquid component.

Example 7

Into SV-110 (manufactured by Nichiden-Rika Glass Co., Ltd.), 9.9 g of the powderizing agent A and 0.1 g of E-Mix D (manufactured by Eisai Co., Ltd.) (vitamin E) were placed. These were kept at 80° C. for 0.5 hours and completely melt for mixing. Here, the amount of the liquid component used was 1% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
  loose bulk density: 0.3 g/cm³
  average particle diameter: 59 μm
  expansion ratio: ×2.1

Figure 3:
FIG. 3 is a view illustrating powder compositions obtained in Examples 7 to 9.

As illustrated in FIG. 3, the powder composition obtained in Example 7 was in the form of powder.

Example 8

Into SV-110 (manufactured by Nichiden-Rika Glass Co., Ltd.), 9.5 g of the powderizing agent A and 0.5 g of E-Mix D (manufactured by Eisai Co., Ltd.) were placed. These were kept at 80° C. for 0.5 hours and completely melt for mixing. Here, the amount of the liquid component used was 5% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
  loose bulk density: 0.3 g/cm³
  average particle diameter: 63 μm
  expansion ratio: ×3.0

As illustrated in FIG. 3, the powder composition obtained in Example 8 was in the form of powder.

Example 9

Into SV-110 (manufactured by Nichiden-Rika Glass Co., Ltd.), 9.0 g of the powderizing agent A and 1.0 g of E-Mix D (manufactured by Eisai Co., Ltd.) were placed. These were kept at 80° C. for 0.5 hours and completely melt for mixing. Here, the amount of the liquid component used was 10% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 69 μm
 expansion ratio: ×1.9

As illustrated in FIG. 3, the powder composition obtained in Example 9 was in the form of powder.

Examples 10 to 13 employed lecithin (hydrophobic phospholipid) as the liquid component.

Example 10

Into SV-110 (manufactured by Nichiden-Rika Glass Co., Ltd.), 9.9 g of the powderizing agent A and 0.1 g of SLP-Paste (lecithin) (manufactured by Tsuji Oil Mill Co., Ltd.) were placed. These were kept at 80° C. for 0.5 hours and completely melt for mixing. Here, the amount of the liquid component used was 1% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 65 μm
 expansion ratio: ×2.5

Figure 4:
FIG. 4 is a view illustrating powder compositions obtained in Examples 10 to 12.

As illustrated in FIG. 4, the powder composition obtained in Example 10 was in the form of powder.

Example 11

Into SV-110 (manufactured by Nichiden-Rika Glass Co., Ltd.), 9.5 g of the powderizing agent A and 0.5 g of SLP-Paste (lecithin) (manufactured by Tsuji Oil Mill Co., Ltd.) were placed. These were kept at 80° C. for 0.5 hours and completely melt for mixing. Here, the amount of the liquid component used was 5% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 69 μm
 expansion ratio: ×2.4

As illustrated in FIG. 4, the powder composition obtained in Example 11 was in the form of powder.

Example 12

Into SV-110 (manufactured by Nichiden-Rika Glass Co., Ltd.), 9.0 g of the powderizing agent A and 1.0 g of SLP-Paste (lecithin) (manufactured by Tsuji Oil Mill Co., Ltd.) were placed. These were kept at 80° C. for 0.5 hours and completely melt for mixing. Here, the amount of the liquid component used was 10% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 75 μm
 expansion ratio: ×2.4

As illustrated in FIG. 4, the powder composition obtained in Example 12 was in the form of powder.

Examples 13 to 15 employed an orange dye (hydrophobic dye) as the liquid component.

Example 13

Into SV-110 (manufactured by Nichiden-Rika Glass Co., Ltd.), 9.9 g of the powderizing agent A and 0.1 g of Orange Color-500-OIL-EX (manufactured by Kiriya Chemical Co., Ltd.) (composition: 60% by mass of capsicum pepper dye (color value 2550), 1% by mass of extracted tocopherol, and 39% by mass of edible oil and/or fat) (extracted tocopherol and edible oil and/or fat are each the solvent of the orange dye) were placed. These were kept at 80° C. for 0.5 hours and completely melt for mixing. Here, the amount of the liquid component used was 1% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 52 μm
 expansion ratio: ×2.8

Figure 5:
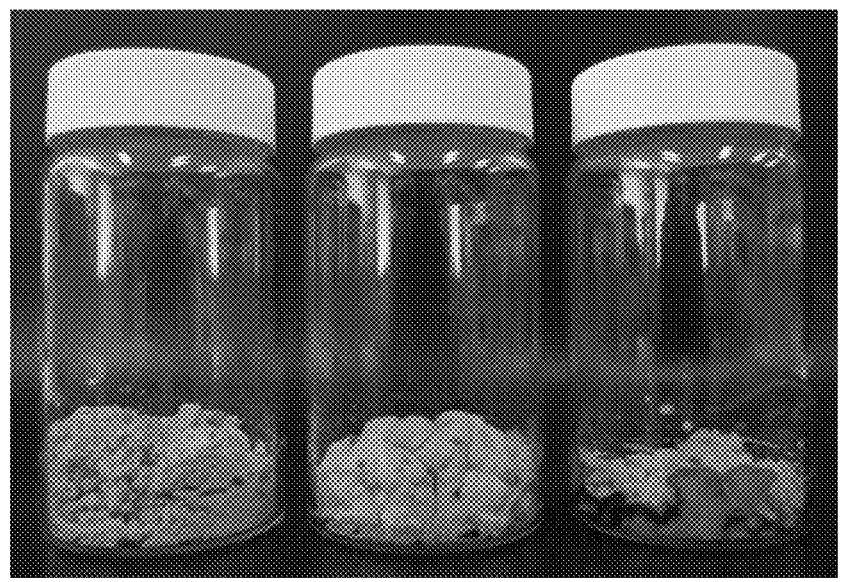
FIG. 5 is a view illustrating powder compositions obtained in Examples 13 to 15.

As illustrated in FIG. 5, the powder composition obtained in Example 13 was in the form of powder.

Example 14

Into SV-110 (manufactured by Nichiden-Rika Glass Co., Ltd.), 9.5 g of the powderizing agent A and 0.5 g of Orange Color-500-OIL-EX (manufactured by Kiriya Chemical Co., Ltd.) (composition: 60% by mass of capsicum pepper dye (color value 2550), 1% by mass of extracted tocopherol, and 39% by mass of edible oil and/or fat) were placed. These were kept at 80° C. for 0.5 hours and completely melt for mixing. Here, the amount of the liquid component used was 5% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 56 μm
 expansion ratio: ×2.4

As illustrated in FIG. 5, the powder composition obtained in Example 14 was in the form of powder.

Example 15

Into SV-110 (manufactured by Nichiden-Rika Glass Co., Ltd.), 9.0 g of the powderizing agent A and 1.0 g of Orange Color-500-OIL-EX (manufactured by Kiriya Chemical Co., Ltd.) (composition: 60% by mass of capsicum pepper dye (color value 2550), 1% by mass of extracted tocopherol, and 39% by mass of edible oil and/or fat) were placed. These were kept at 80° C. for 0.5 hours and completely melt for mixing. Here, the amount of the liquid component used was 10% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 61 μm
 expansion ratio: ×1.6

As illustrated in FIG. 5, the powder composition obtained in Example 15 was in the form of powder.

Examples 16 to 18 employed an orange dye (hydrophilic dye) as the liquid component.

Example 16

Into SV-110 (manufactured by Nichiden-Rika Glass Co., Ltd.), 9.9 g of the powderizing agent A and 0.1 g of Orange Color 75 WS (manufactured by Kiriya Chemical Co., Ltd.) (composition: 15% by mass of capsicum pepper dye (color value 1400), 21.2% by mass of purified water, 55% by mass of glycerin, 4% by mass of glycerin fatty acid ester, 4% by mass of sucrose fatty acid ester, and 0.8% by mass of extracted tocopherol) (purified water and glycerin are each the solvent of orange dye, glycerin fatty acid ester and sucrose fatty acid ester are each an emulsifier, and extracted tocopherol is an antioxidant) were placed. These were kept at 80° C. for 0.5 hours and completely melt for mixing. Here, the amount of the liquid component used was 1% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 59 μm
 expansion ratio: ×2.1

Figure 6:
FIG. 6 is a view illustrating powder compositions obtained in Examples 16 to 18.

As illustrated in FIG. 6, the powder composition obtained in Example 16 was in the form of powder.

Example 17

Into SV-110 (manufactured by Nichiden-Rika Glass Co., Ltd.), 9.5 g of the powderizing agent A and 0.5 g of Orange Color 75 WS (manufactured by Kiriya Chemical Co., Ltd.) (composition: 15% by mass of capsicum pepper dye (color value 1400), 21.2% by mass of purified water, 55% by mass of glycerin, 4% by mass of glycerin fatty acid ester, 4% by mass of sucrose fatty acid ester, and 0.8% by mass of extracted tocopherol) were placed. These were kept at 80° C. for 0.5 hours and completely melt for mixing. Here, the amount of the liquid component used was 5% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 63 μm
 expansion ratio: ×2.1

As illustrated in FIG. 6, the powder composition obtained in Example 17 was in the form of powder.

Example 18

Into SV-110 (manufactured by Nichiden-Rika Glass Co., Ltd.), 9.0 g of the powderizing agent A and 1.0 g of Orange Color 75 WS (manufactured by Kiriya Chemical Co., Ltd.) (composition: 15% by mass of capsicum pepper dye (color value 1400), 21.2% by mass of purified water, 55% by mass of glycerin, 4% by mass of glycerin fatty acid ester, 4% by mass of sucrose fatty acid ester, and 0.8% by mass of extracted tocopherol) were placed. These were kept at 80° C. for 0.5 hours and completely melt for mixing. Here, the amount of the liquid component used was 10% by mass relative to the total mass of the powder composition (powderizing agent A+liquid component). Next, the mixture was cooled in a 60° C.-thermostatic chamber for 12 hours to form a solid having voids with an increased volume. After the crystallization was completed, cooling was performed to the room temperature (25° C.) state. A powder-form crystalline composition was obtained by loosening the obtained solid.

The characteristics of the obtained powder composition were as follows.
 loose bulk density: 0.3 g/cm$^3$
 average particle diameter: 70 μm
 expansion ratio: ×2.3

As illustrated in FIG. 6, the powder composition obtained in Example 18 was in the form of powder.

Examples 19 to 23 employed lecithin (hydrophobic phospholipid) as the liquid component.

Example 19

After 9.9 g of powderizing agent A' and 0.1 g of SLP-Paste (manufactured by Tsuji Oil Mill Co., Ltd.) (lecithin) were placed into SV-110 (manufactured by Nichiden-Rika Glass Co., Ltd.), these were completely mixed at 20° C. Here, the amount of the liquid component used was 1% by mass relative to the total mass of the powder composition (powderizing agent A'+liquid component).

Figure 7:
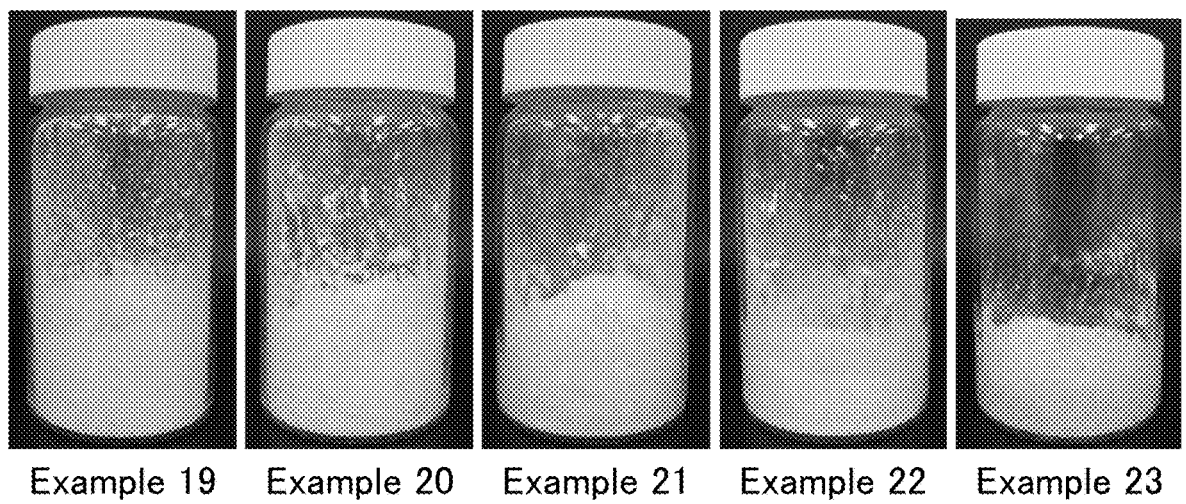
FIG. 7 is a view illustrating powder compositions obtained in Examples 19 to 23.

The characteristics of the obtained powder composition were as follows.
loose bulk density: 0.3 g/cm$^3$
average particle diameter: 69 μm As illustrated in FIG. 7, the powder composition obtained in Example 19 was in the form of powder.

Example 20

After 9.5 g of powderizing agent A' and 0.5 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 5% by mass relative to the total mass of the powder composition (powderizing agent A'+liquid component).

The characteristics of the obtained powder composition were as follows.
loose bulk density: 0.3 g/cm$^3$
average particle diameter: 70 μm As illustrated in FIG. 7, the powder composition obtained in Example 20 was in the form of powder.

Example 21

After 9.0 g of powderizing agent A' and 1.0 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 10% by mass relative to the total mass of the powder composition (powderizing agent A'+liquid component).

The characteristics of the obtained powder composition were as follows.
loose bulk density: 0.3 g/cm$^3$
average particle diameter: 78 μm As illustrated in FIG. 7, the powder composition obtained in Example 21 was in the form of powder.

Example 22

After 8.0 g of powderizing agent A' and 2.0 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 20% by mass relative to the total mass of the powder composition (powderizing agent A'+liquid component).

The characteristics of the obtained powder composition were as follows.
loose bulk density: 0.4 g/cm$^3$
average particle diameter: 132 μm As illustrated in FIG. 7, the powder composition obtained in Example 22 was in the form of powder.

Example 23

After 7.0 g of powderizing agent A' and 3.0 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 30% by mass relative to the total mass of the powder composition (powderizing agent A'+liquid component).

The characteristics of the obtained powder composition were as follows.
loose bulk density: 0.4 g/cm$^3$
average particle diameter: 189 μm As illustrated in FIG. 7, the powder composition obtained in Example 23 was in the form of powder.

Table 2 summarizes the results of Examples described above.

TABLE 2

| | Name of Functional Material | Property of Liquid Component | Amount of Liquid Component Used (% by Mass) | Powderizing Agent | Number of Carbon Atoms x | XXX-Type Triglyceride (% by Mass) | Loose Bulk Density (g/cm3) | Average Particle Diameter (μm) | Expansion Ratio (Times) | Final Cooling Temperature/ Hour |
|---|---|---|---|---|---|---|---|---|---|---|
| Example 1 | Locust Garlic Oil | Hydrophobic | 1.0 | A | 18 | 79.1 | 0.3 | 58 | 2.5 | 60° C./12 Hours |
| Example 2 | Locust Garlic Oil | Hydrophobic | 5.0 | A | 18 | 79.1 | 0.3 | 62 | 2.4 | 60° C./12 Hours |
| Example 3 | Locust Garlic Oil | Hydrophobic | 10.0 | A | 18 | 79.1 | 0.3 | 67 | 1.9 | 60° C./12 Hours |
| Example 4 | Shrimp Flavor | Hydrophilic | 1.0 | A | 18 | 79.1 | 0.3 | 60 | 2.8 | 60° C./12 Hours |
| Example 5 | Shrimp Flavor | Hydrophilic | 5.0 | A | 18 | 79.1 | 0.3 | 64 | 2.5 | 60° C./12 Hours |
| Example 6 | Shrimp Flavor | Hydrophilic | 10.0 | A | 18 | 79.1 | 0.3 | 70 | 2.2 | 60° C./12 Hours |
| Example 7 | Vitamin E | Hydrophobic | 1.0 | A | 18 | 79.1 | 0.3 | 59 | 2.1 | 60° C./12 Hours |
| Example 8 | Vitamin E | Hydrophobic | 5.0 | A | 18 | 79.1 | 0.3 | 63 | 3.0 | 60° C./12 Hours |
| Example 9 | Vitamin E | Hydrophobic | 10.0 | A | 18 | 79.1 | 0.3 | 69 | 1.9 | 60° C./12 Hours |

TABLE 2-continued

| Name of Functional Material | Property of Liquid Component | Amount of Liquid Component Used (% by Mass) | Powderizing Agent | Number of Carbon Atoms x | XXX-Type Triglyceride (% by Mass) | Loose Bulk Density (g/cm3) | Average Particle Diameter (μm) | Expansion Ratio (Times) | Final Cooling Temperature/ Hour |
|---|---|---|---|---|---|---|---|---|---|
| Example 10 | Lecithin | Hydrophobic | 1.0 | A | 18 | 79.1 | 0.3 | 65 | 2.5 | 60° C./12 Hours |
| Example 11 | Lecithin | Hydrophobic | 5.0 | A | 18 | 79.1 | 0.3 | 69 | 2.4 | 60° C./12 Hours |
| Example 12 | Lecithin | Hydrophobic | 10.0 | A | 18 | 79.1 | 0.3 | 75 | 2.4 | 60° C./12 Hours |
| Example 13 | Orange Dye | Hydrophobic | 1.0 | A | 18 | 79.1 | 0.3 | 52 | 2.8 | 60° C./12 Hours |
| Example 14 | Orange Dye | Hydrophobic | 5.0 | A | 18 | 79.1 | 0.3 | 56 | 2.4 | 60° C./12 Hours |
| Example 15 | Orange Dye | Hydrophobic | 10.0 | A | 18 | 79.1 | 0.3 | 61 | 1.6 | 60° C./12 Hours |
| Example 16 | Orange Dye | Hydrophilic | 1.0 | A | 18 | 79.1 | 0.3 | 59 | 2.1 | 60° C./12 Hours |
| Example 17 | Orange Dye | Hydrophilic | 5.0 | A | 18 | 79.1 | 0.3 | 63 | 2.1 | 60° C./12 Hours |
| Example 18 | Orange Dye | Hydrophilic | 10.0 | A | 18 | 79.1 | 0.3 | 70 | 2.3 | 60° C./12 Hours |
| Example 19 | Lecithin | Hydrophobic | 1.0 | A' | 18 | 79.1 | 0.3 | 69 | — | — |
| Example 20 | Lecithin | Hydrophobic | 5.0 | A' | 18 | 79.1 | 0.3 | 70 | — | — |
| Example 21 | Lecithin | Hydrophobic | 10.0 | A' | 18 | 79.1 | 0.3 | 78 | — | — |
| Example 22 | Lecithin | Hydrophobic | 20.0 | A' | 18 | 79.1 | 0.4 | 132 | — | — |
| Example 23 | Lecithin | Hydrophobic | 30.0 | A' | 18 | 79.1 | 0.4 | 189 | — | — |

INDUSTRIAL APPLICABILITY

The present invention is applicable to various fields of, for example, foods, pharmaceuticals, agriculture, and industry.

The invention claimed is:

1. A powderizing agent for a liquid component, wherein the powderizing agent contains an oil and/or fat composition,
the oil and/or fat composition contains an oil and/or fat component which contains one or more types of XXX-type triglycerides having fatty acid residues X, each with x carbon atoms, at positions 1 to 3 of glycerin,
x, the number of carbon atoms, is an integer selected from 10 to 22,
the XXX-type triglyceride is contained at 50% by mass or more relative to a content of the oil and/or fat component being 100% by mass,
the oil and/or fat composition is a powder oil and/or fat composition,
the oil and/or fat component contains a β-type oil and/or fat,
a particle of the powder oil and/or fat composition has a plate shape, and
the liquid component is a liquid at 20° C.

2. The powderizing agent according to claim 1, wherein a loose bulk density of the powder oil and/or fat composition is 0.05 to 0.6 g/cm³.

3. The powderizing agent according to claim 1, wherein the liquid component contains a hydrophobic substance.

4. The powderizing agent according to claim 1, wherein the liquid component is a solution of a hydrophobic substance.

5. The powderizing agent according to claim 1, wherein the liquid component is an emulsion of a hydrophobic substance.

6. The powderizing agent according to claim 3, wherein the hydrophobic substance is selected from the group consisting of flavors, dyes, vitamins, lipids, and mixtures thereof.

7. The powderizing agent according to claim 1, wherein the liquid component contains a hydrophilic substance.

8. The powderizing agent according to claim 1, wherein the liquid component is a solution of a hydrophilic substance.

9. The powderizing agent according to claim 1, wherein the liquid component is an emulsion of a hydrophilic substance.

10. The powderizing agent according to claim 9, wherein the hydrophilic substance is selected from the group consisting of flavors, dyes, vitamins, and mixtures thereof.

11. The powderizing agent according to claim 1, wherein the liquid component is a liquid form food.

12. The powderizing agent according to claim 11, wherein the liquid form food is selected from the group consisting of cow's milk, wines, fruit juices, stock, and yogurts.

13. A method of producing a powder composition, comprising:
a mixing step of mixing a powderizing agent and a liquid component,
wherein the powderizing agent contains an oil and/or fat composition,
the oil and/or fat composition contains an oil and/or fat component which contains one or more types of XXX-type triglycerides having fatty acid residues X, each with x carbon atoms, at positions 1 to 3 of glycerin, x, the number of carbon atoms, is an integer selected from 10 to 22, the XXX-type triglyceride is contained at 50% by mass or more relative to a content of the oil and/or fat component being 100% by mass, the oil and/or fat composition is a powder oil and/or fat composition, the oil and/or fat component contains a β-type oil and/or fat, and a particle of the powder oil and/or fat composition has a plate shape, and wherein the liquid component is a liquid at 20° C.

14. The production method according to claim 13, further comprising a cooling step of cooling a mixture of the powderizing agent and the liquid component.

15. The production method according to claim 14, wherein a cooling temperature in the cooling step is equal to or higher than a temperature calculated by the following formula: cooling temperature (° C.)=number of carbon atoms x×6.6-68.

16. The production method according to claim 15, wherein the oil and/or fat component contains a β-type oil and/or fat, and the cooling temperature is a temperature lower than a melting point of the β-type oil and/or fat.

17. The production method according to claim 14, wherein a seeding process, a tempering process, and/or a pre-cooling process are further performed between the mixing step and the cooling step.

18. The production method according to claim 13, wherein an amount of the liquid component used is 0.1 to 30% by mass relative to a total mass of the powder composition.

19. A powder composition comprising the powderizing agent according to a claim 1 and a liquid component, wherein the liquid component is a liquid at 20° C.

20. A food and/or beverage comprising the powder composition according to claim 19.

* * * * *